(12) United States Patent
Yates et al.

(10) Patent No.: US 9,834,525 B2
(45) Date of Patent: Dec. 5, 2017

(54) INHIBITORS OF PAXILLIN FUNCTION AND RELATED COMPOSITIONS AND METHODS

(71) Applicants: UNIVERSITY OF TENNESSEE RESEARCH FOUNDATION, Memphis, TN (US); Bilal Abou Aleiwi, Memphis, TN (US)

(72) Inventors: Charles Ryan Yates, Collierville, TN (US); Duane D. Miller, Collierville, TN (US); Frank Park, Memphis, TN (US); Jordan J. Toutounchian, Memphis, TN (US); Vanessa Morales-Tirado, Memphis, TN (US); Shivaputra Patil, Lake Bluff, IL (US); Jayaprakash Pagadala, Memphis, TN (US); Bilal Abou Aleiwi, Memphis, TN (US)

(73) Assignee: UNIVERSITY OF TENNESSEE RESEARCH FOUNDATION, MEMPHIS, TN (US)

(*) Notice: Subject to any disclaimer, the term of this patent is extended or adjusted under 35 U.S.C. 154(b) by 0 days.

(21) Appl. No.: 15/116,764

(22) PCT Filed: Feb. 4, 2015

(86) PCT No.: PCT/US2015/014473
§ 371 (c)(1),
(2) Date: Aug. 4, 2016

(87) PCT Pub. No.: WO2015/120059
PCT Pub. Date: Aug. 13, 2015

(65) Prior Publication Data
US 2016/0347725 A1 Dec. 1, 2016

(51) Int. Cl.
| | | |
|---|---|---|
| *C07D 265/18* | (2006.01) | |
| *C07D 211/84* | (2006.01) | |
| *C07D 215/36* | (2006.01) | |
| *C07D 239/82* | (2006.01) | |
| *C07D 265/12* | (2006.01) | |
| *C07D 498/04* | (2006.01) | |
| *A61K 47/14* | (2017.01) | |
| *C07D 221/10* | (2006.01) | |
| *A61K 9/00* | (2006.01) | |
| *A61K 9/107* | (2006.01) | |

(52) U.S. Cl.
CPC ......... *C07D 265/18* (2013.01); *C07D 211/84* (2013.01); *C07D 215/36* (2013.01); *C07D 221/10* (2013.01); *C07D 239/82* (2013.01); *C07D 265/12* (2013.01); *C07D 498/04* (2013.01); *A61K 9/0048* (2013.01); *A61K 9/1075* (2013.01); *A61K 47/14* (2013.01)

(58) Field of Classification Search
CPC .. C07D 265/18; C07D 211/84; C07D 215/36; C07D 221/10; C07D 239/82; C07D 265/12; C07D 498/04; A61K 9/0048; A61K 9/1075; A61K 47/14
USPC ...................................................... 514/229.8
See application file for complete search history.

(56) References Cited

U.S. PATENT DOCUMENTS

| | | | |
|---|---|---|---|
| 3,400,119 A | 9/1968 | Wilhelm et al. | |
| 3,467,656 A * | 9/1969 | Metlesics ............. | C07D 265/18 514/837 |
| 3,925,549 A * | 12/1975 | Ott ....................... | C07D 239/78 514/266.31 |
| 4,518,597 A | 5/1985 | Narr et al. | |
| 2010/0160304 A1 | 6/2010 | Katayama | |

FOREIGN PATENT DOCUMENTS

| | | |
|---|---|---|
| DE | 1932401 A1 | 1/1970 |
| DE | 2656156 A1 | 6/1977 |
| DE | 2838846 A1 | 3/1979 |
| DE | 3217012 A1 | 11/1983 |
| EP | 0 564 397 A1 | 10/1993 |
| GB | 1265548 A | 3/1972 |
| GB | 1510270 A | 5/1978 |
| GB | 2018761 A | 10/1979 |
| NL | 6604470 A | 10/1966 |
| WO | 2006/010142 A2 | 1/2006 |
| WO | 2006/048308 A1 | 5/2006 |
| WO | 2006/077821 A1 | 7/2006 |
| WO | 2011/034896 A2 | 3/2011 |
| WO | 2014/012050 A2 | 1/2014 |

OTHER PUBLICATIONS

Kobayashi et al. Tetrahedron, 2010, 66, 9336-9339.*
Mamaev et al. Khimiya Geterotsiklicheskih Soedinenii, 1965, 4, 608-15.*
Gawad et al. European Journal of Medicinal Chemistry, 2010, 45, 6058-6067.*
Kobayashi et al Tetrahedron, 2010, 66, 9336-9339.*
De Marchi et al. (1971) "Synthesis and Pharmacological Evaluation of 1,4-Dihydro-2H-3,1-benzoxazin-2-one Derivatives," J. Pharm. Sci. 60(11):1757-1759.
Hernandez et al. (2007) "Synthesis of 1,4-dihydro-benzo[d][1,3]oxazin-2-ones from phthalides via an aminolysis-Hofmann rearrangement protocol," Tetrahedron Letters. 48(51):8972-8975.
Lednicer et al. (1971) "Preparation of indoles from 4H-3,1-benzothiazines by extrusion of sulfur," Hetrocyclic Chemistry. 8(6):903-910.
Mamaev et al. (1965) "Pyrimidines. III. Dehydrogenation of 4-phenylbenzo[h]quinazoline derivatives," Khimiya Geterotsiklicheskikh Soedinenii. 1965(4):608-615.—Abstract provided only from the Scientific and Technical Information Network, A Chemical Abstracts Service. STN Accession No. 64:27547.

(Continued)

Primary Examiner — Yevegeny Valenrod
(74) Attorney, Agent, or Firm — Brian C. Trinque; Lathrop Gage LLP

(57) ABSTRACT

This disclosure relates to small molecule inhibitors of paxillin and paxillin binding, and related compositions and methods of treatment.

18 Claims, 29 Drawing Sheets

(56) References Cited

OTHER PUBLICATIONS

Mikhaleva et al. (1976) "[Pyrimidines. LIV. Synthesis of 3-oxobenzo[f]quinazolines]," Izvestiya Sibirskogo Otdeleniya Akademii Nauk SSSR. 1976(4):129-131.—Abstract provided only from the Scientific and Technical Information Network, A Chemical Abstracts Service. STN Accession No. 85:160018.

Muchowski et al. (1980) "Ortho functionalization of N-(tert-butoxycarbonyl)aniline," J. Org. Chem. 45(23):4798-4801.

Pflegel et al. (1982) "[Polarography of heterocyclics. 14. Polarography of 7-chloro-5-phenyl-2-thioxo-1H-2,3-dihydro-1,3,4-benzotriazepines],," Pharmazie. 37(10):714-717.—Abstract provided only from the Scientific and Technical Information Network, A Chemical Abstracts Service. STN Accession No. 98:126047.

Testa et al. (1966) "[Substance active on the center nervous system. XLVII. 1. Synthesis of 4-phenyl-6-chloro-4H-3,1-benzoxazin-2-(1H)one and derivatives]," Farmaco. 21(8):549-557.—Abstract provided only from the Scientific and Technical Information Network, A Chemical Abstracts Service. STN Accession No. 66:28719.

International Search Report with Written Opinion corresponding to International Patent Application No. PCT/US2015/014473, dated May 21, 2015.

* cited by examiner

FIGURE 7

| Test article | Test Species | Test Conc. | NADPH | Parent remaining | | |
|---|---|---|---|---|---|---|
| | | | | 1st (%) | 2nd (%) | Mean (%) |
| Compound (II-4) | Human | 1 μM | Yes | 37.5 | 41.8 | 39.7 |
| | | | No | 106.9 | 101.4 | 103.7 |
| | Mouse | 1 μM | Yes | 2.8 | 2.5 | 2.7 |
| | | | No | 99.5 | 99.6 | 99.6 |
| | Rat | 1 μM | Yes | 0.3 | 0.1 | 0.2 |
| | | | No | 102.6 | 116.1 | 109.4 |

FIGURE 8

% Inhibition of CYP450 Enzymes:  Compound (II-4) vs. Positive Control Inhibitors

| Inhibitor | CYP3A4 (ketoconazole) | CYP2C9 (sulphaphenazole) | CYP2D6 (quinidine) | CYP2C19 (ticlopidine) | CYP1A2 (α-naphthoflavone) |
|---|---|---|---|---|---|
| Control | 95.3% | 87.6% | 91.9% | 95.7% | 93.8% |
| Compound (II-4) | 5.2% | 39.9% | 14.5% | 31.8% | 12.4% |

FIGURE 9
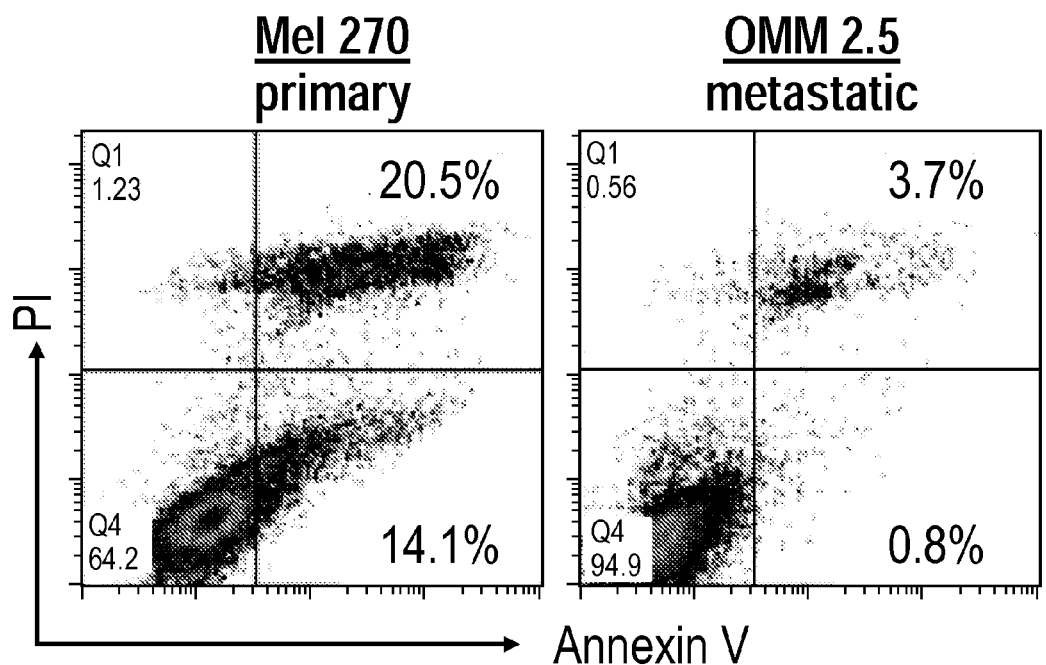
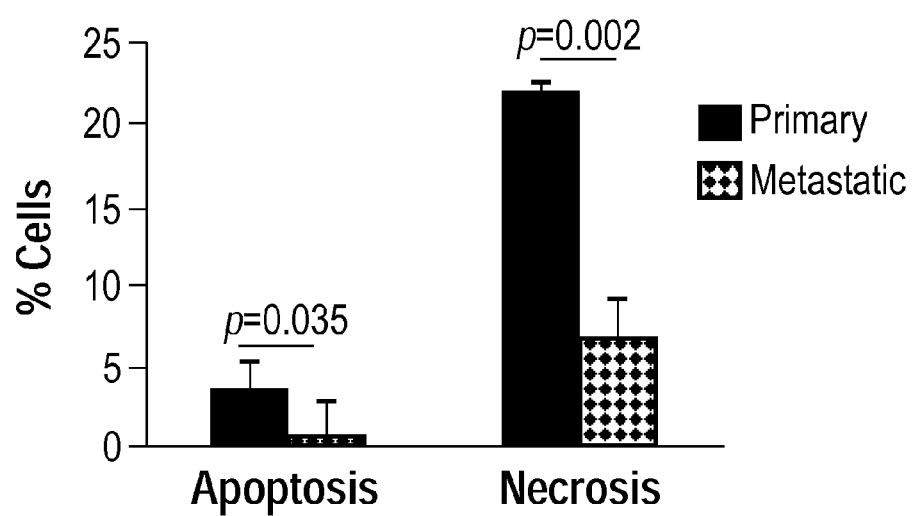

FIGURE 10

| Gene | Fold difference UM-metastatic relative to UM-primary tumor cells |
|---|---|
| COL4A2 – Type IV Collage | 42 |
| TNC – Tenascin C | 36 |
| SRC – v-src Sarcoma Viral Oncogene Homolog | 8 |
| MCAM – Melanoma Cell Adhesion Molecule/ MUC18 | 4 |
| TGFB1 – Transforming Growth Factor beta | 2 |
| VEGFA – Vascular Endothelial Growth Factor A | 2 |
| MTSS1 – Metastasis suppressor 1 | 2 |
| TP53 – Tumor Protein 53 | 2 |

FIGURE 11

| Gene | Fold difference UM-metastatic relative to UM-primary tumor cells |
|---|---|
| KISS1R – Kisspeptin Receptor | 209 |
| KISS1 – Kisspeptin | 181 |
| CDH1 – Epithelial Cadherin | 181 |
| FXYD5 – FXYD domain-containing ion transport regulator 5 | 87 |
| MMP7 – Matrix Metalloproteinase 7 | 86 |
| TNFSF10 – Tumor Necrosis Factor (Ligand) Superfamily, Member 10 | 76 |
| MMP10 – Matrix Metalloproteinase 10 | 58 |
| MMP2 – Matrix Metalloproteinase 2 | 58 |
| RORB – Related Orphan Receptor B | 52 |
| CCL7 – Chemokine (C-C) ligand 7 | 48 |
| HGF – Hepatocyte Growth Factor | 47 |
| CXCR2 – Chemokine (C-X-C) receptor 2 | 47 |
| MMP3 – Matrix Metalloproteinase 3 | 43 |
| IL18 – Interleukin 18 | 33 |
| CXCL12 – Chemokine (C-X-C) ligand 12 | 33 |
| MMP9 – Matrix Metalloproteinase 9 | 33 |
| MMP11 – Matrix Metalloproteinase 11 | 19 |
| CXCR4 – Chemokine (C-X-C) receptor 4 | 19 |
| MYCL1 – v-Myc Myelocytomatosis Viral Oncogne Homolog 1 | 12 |
| PECAM1 – Platelet Endothelial Cell Adhesion Molecule | 10 |
| SELE – Selectin E | 10 |
| ITGA4 – alpha-4 subunit | 8 |

FIGURE 12
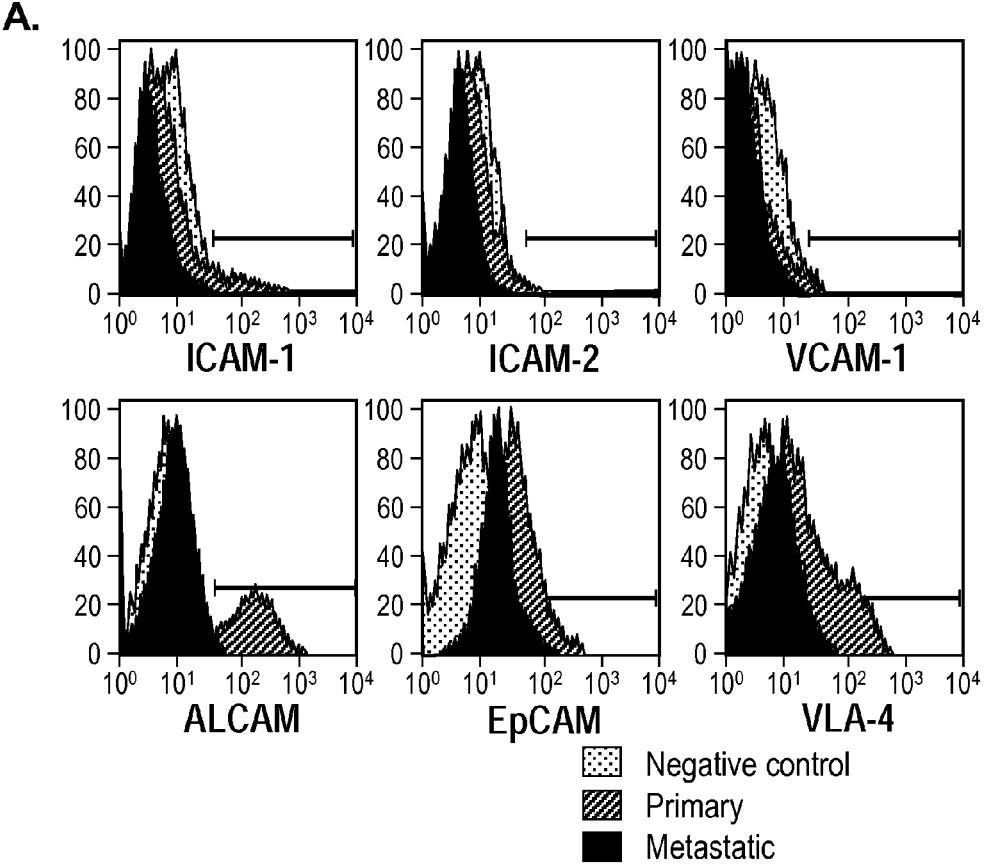
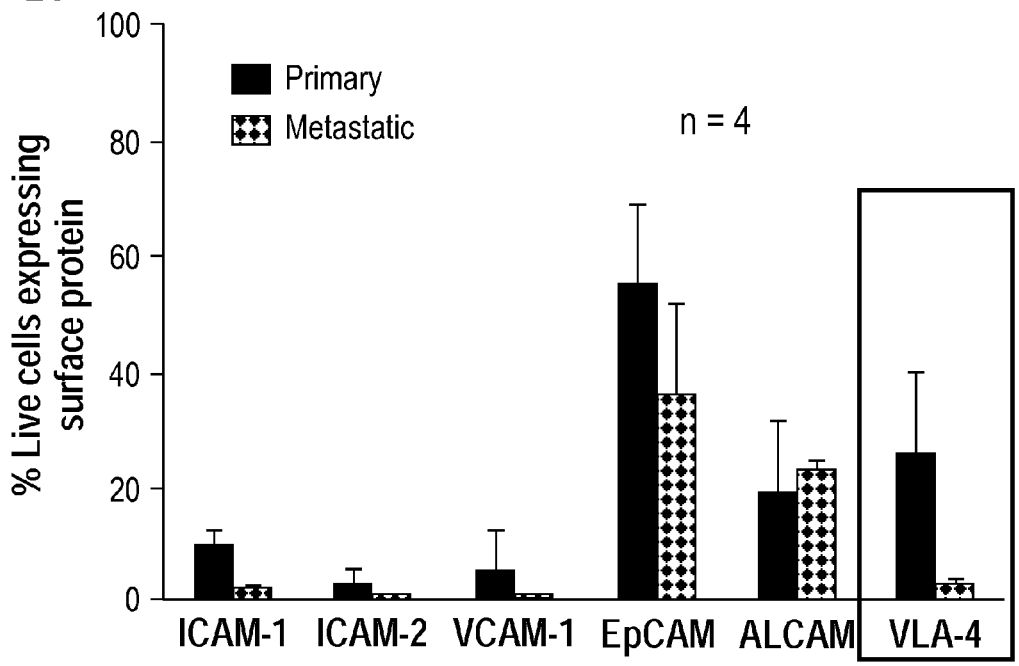

FIGURE 12
C.
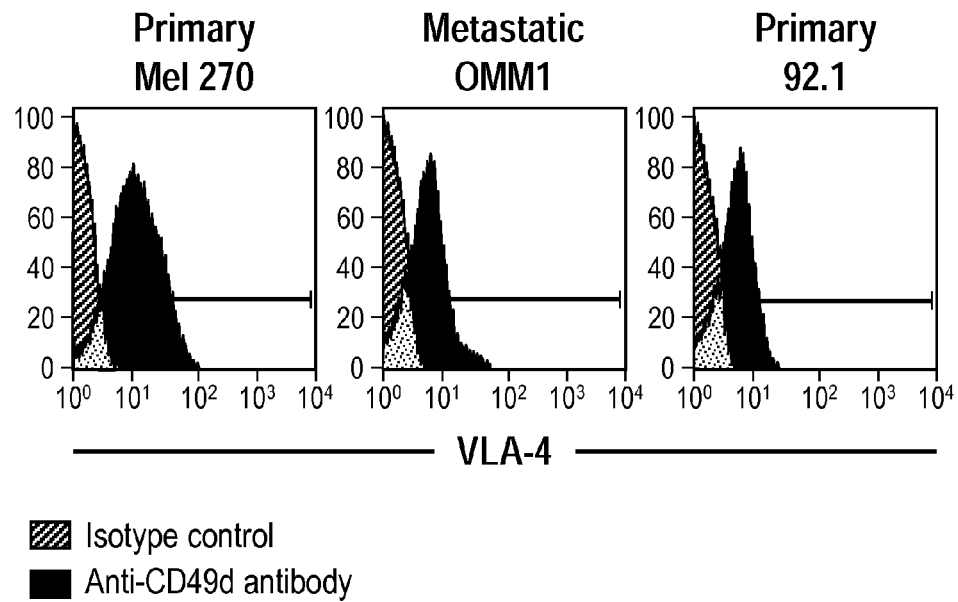
D.
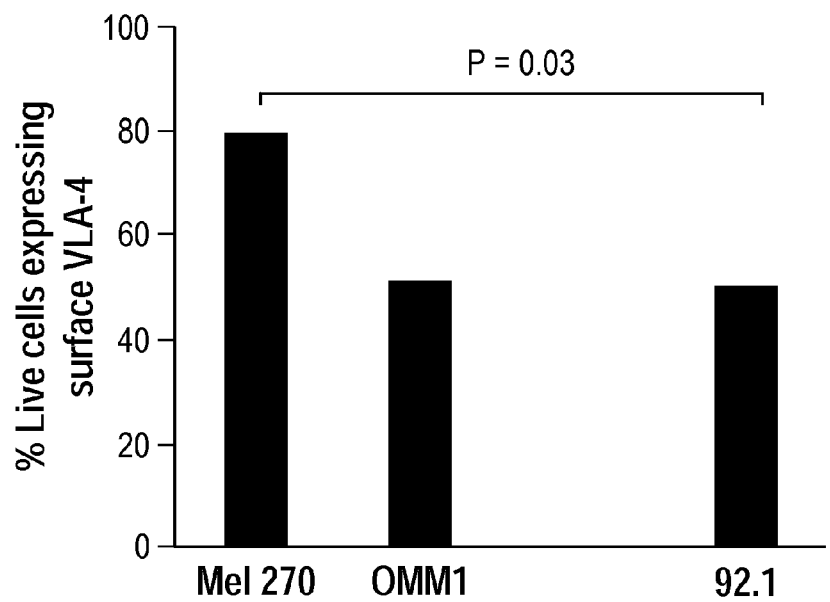

FIGURE 13
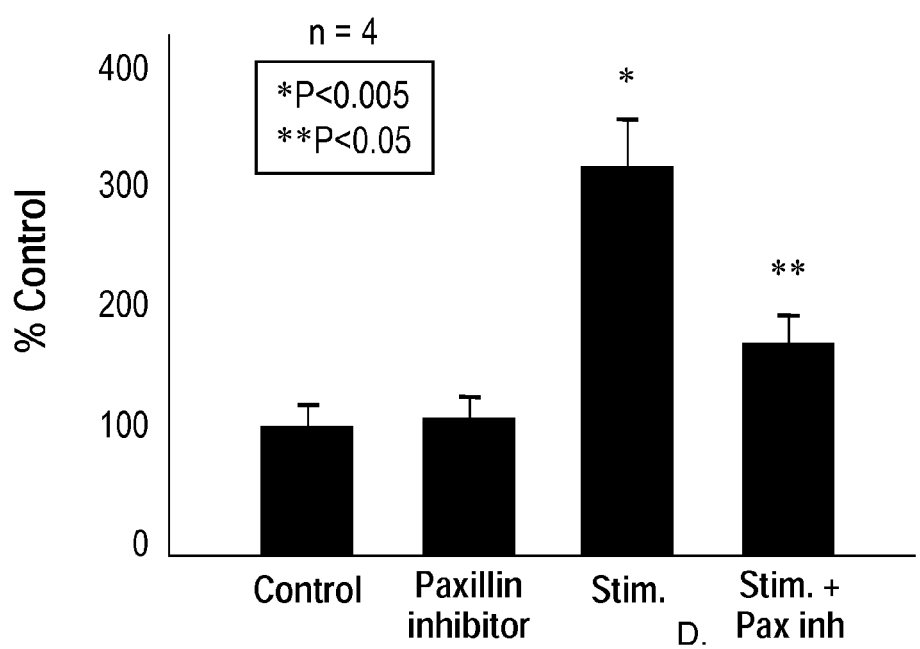
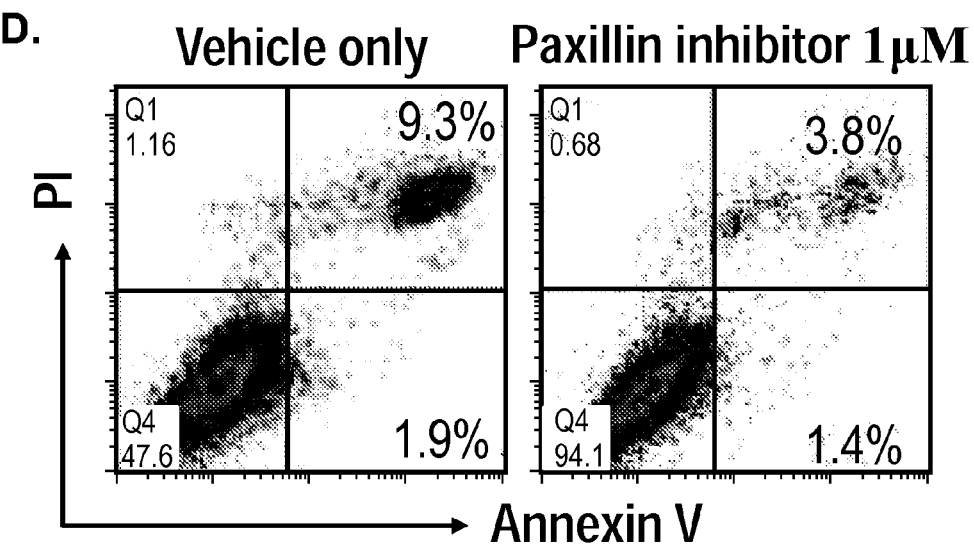

FIGURE 14
A.
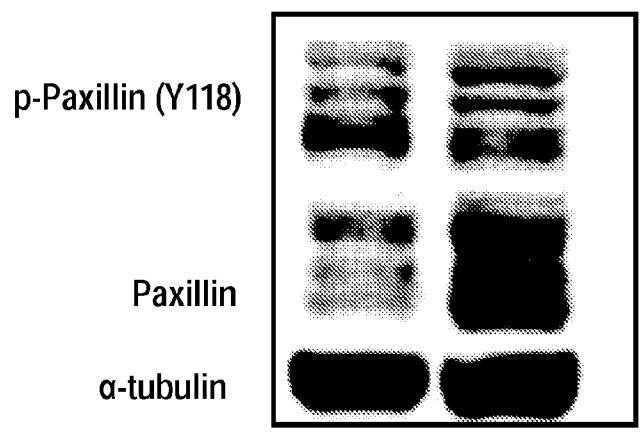
B.
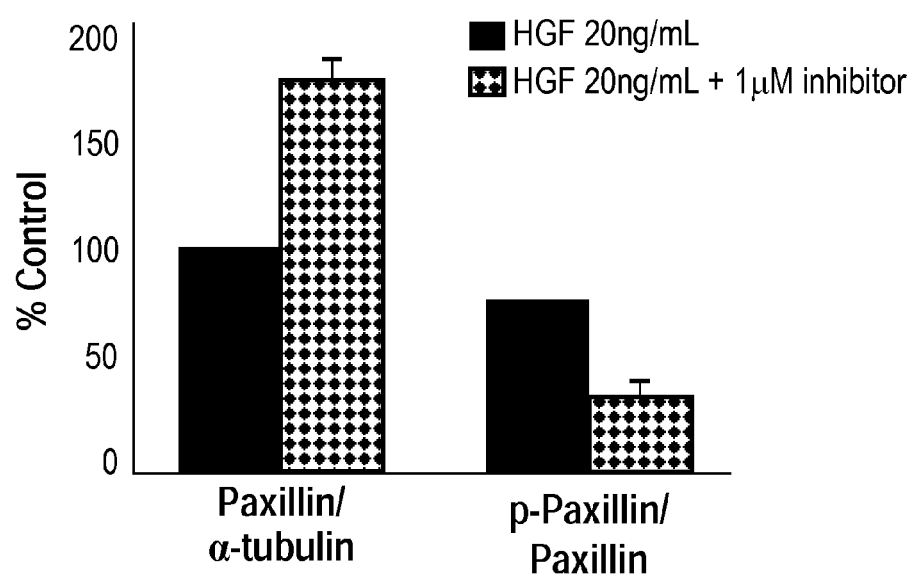

FIGURE 15
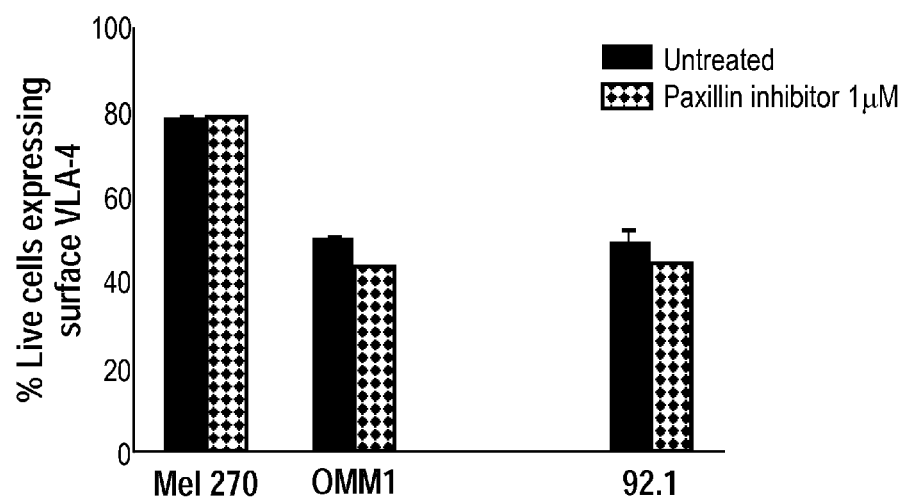
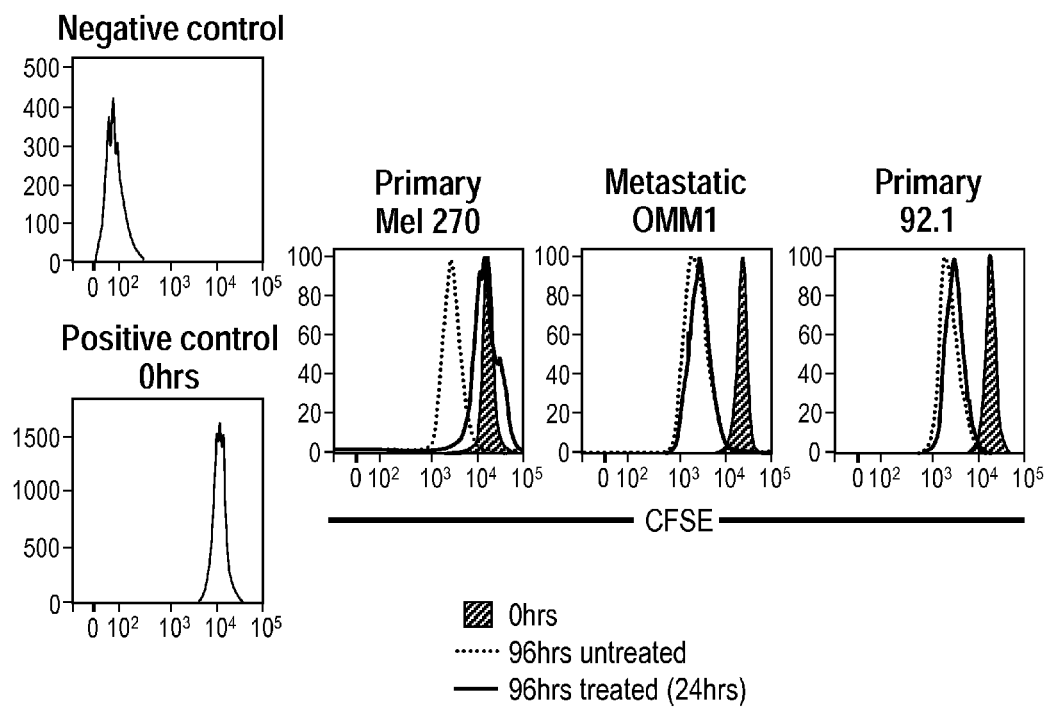

FIGURE 16
A.
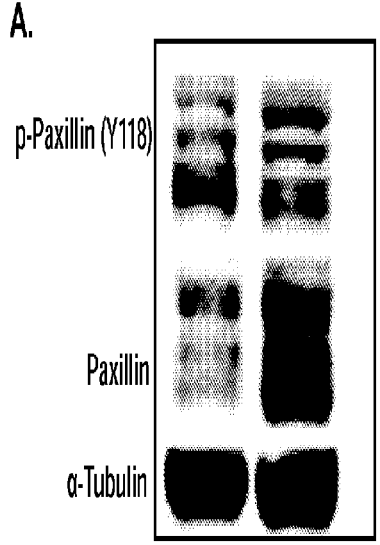
B.
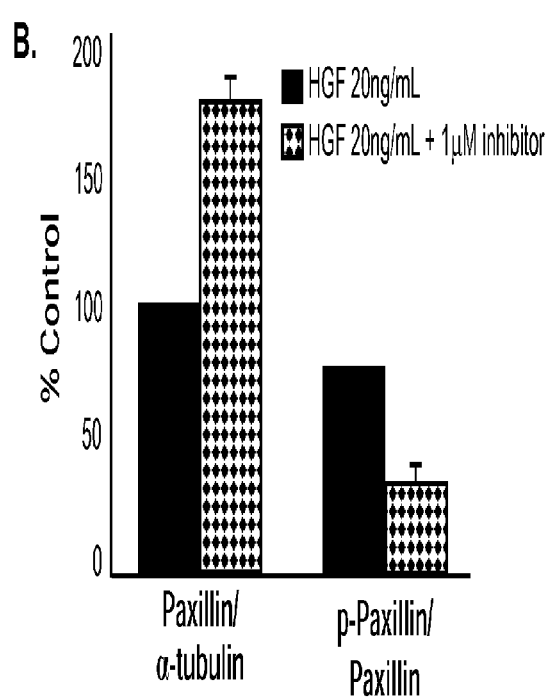
C.
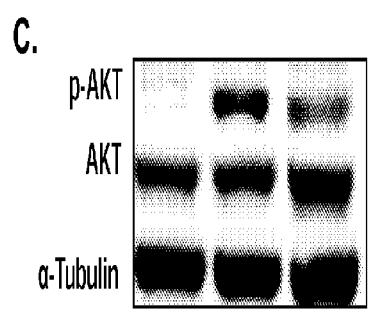
D.
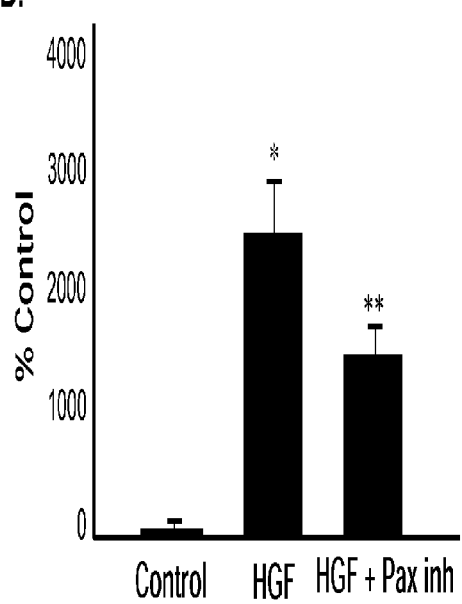

FIGURE 17
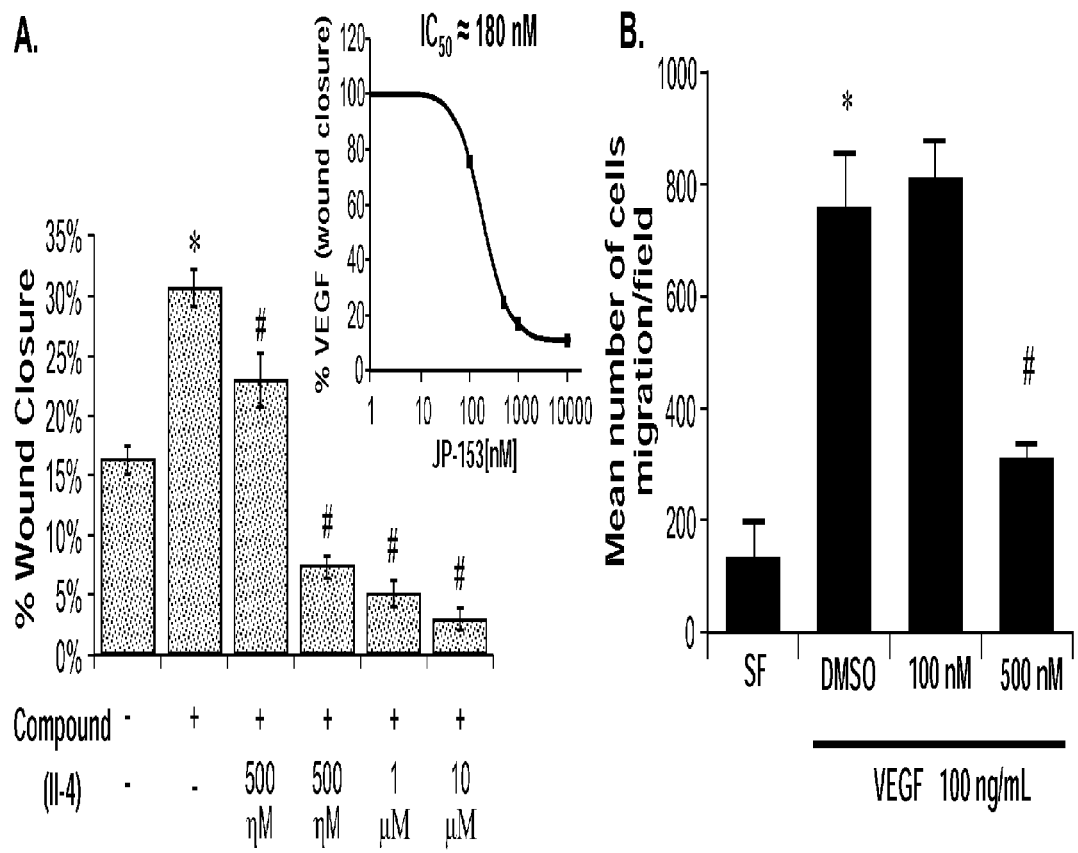
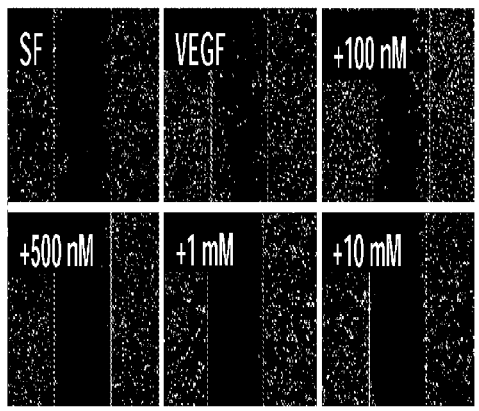
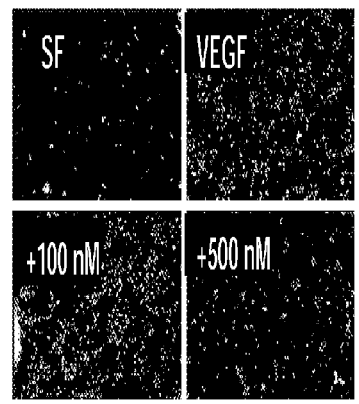

FIGURE 18
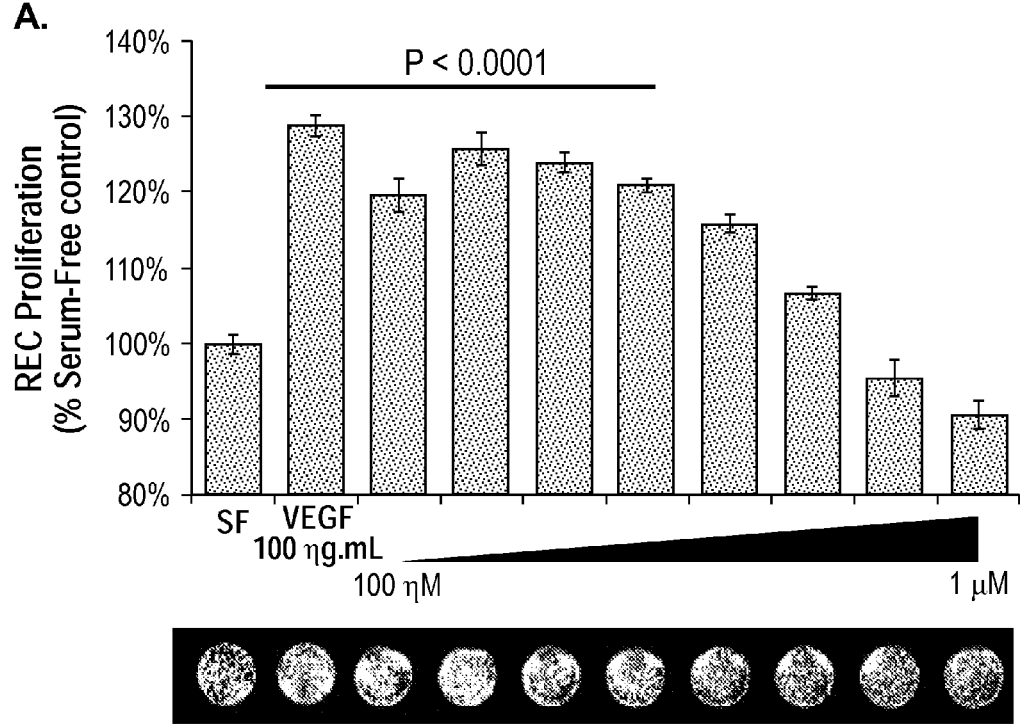
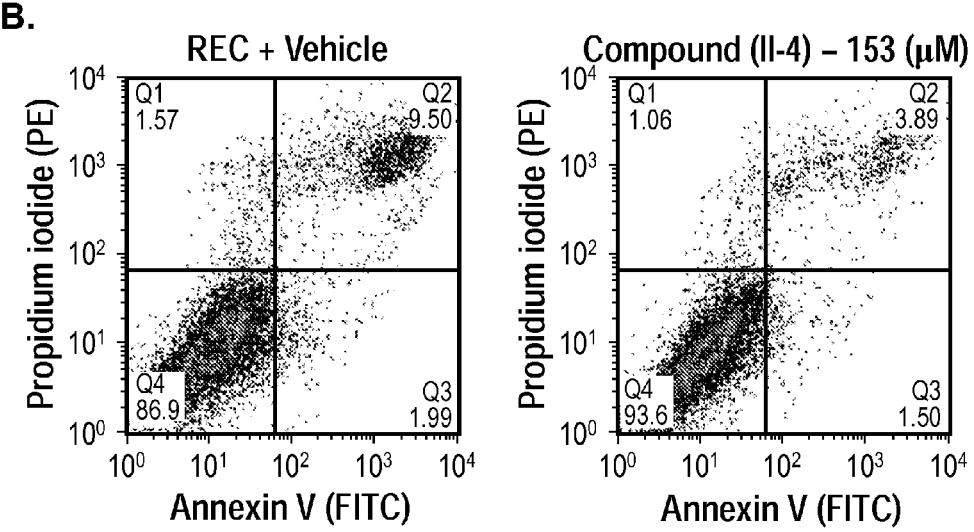

FIGURE 23

| Test Article | Test Species | Test Conc. | NADPH | Parent Remaining | | |
|---|---|---|---|---|---|---|
| | | | | 1st (%) | 2nd (%) | Mean (%) |
| Compound (II-4) | Human | 1 µM | Yes | 37.5 | 41.8 | 39.7 |
| | | | No | 106.9 | 101.4 | 103.7 |
| | Mouse | 1 µM | Yes | 2.8 | 2.5 | 2.7 |
| | | | No | 99.5 | 99.6 | 99.6 |
| | Rat | 1 µM | Yes | 0.3 | 0.1 | 0.2 |
| | | | No | 102.6 | 116.1 | 109.4 |

FIGURE 24

| | %Inhibition of CYP450 Enzymes: (II-4) vs. Positive Control Inhibitors | | | | |
|---|---|---|---|---|---|
| Inhibitor | CYP3A4 (ketoconazole) | CYP2C9 (sulphaphenazole) | CYP2D6 (quinidine) | CYP2C19 (ticlopidine) | CYP1A2 (α-naphthoflavone) |
| Control | 95% | 88% | 92% | 96% | 94% |
| Compound (II-4) | 5% | 40% | 15% | 32% | 12% |

FIGURE 25

| Compound (II-4) [10μM] | |
|---|---|
| 5-HT$_{2B}$ | 75.5% |
| MT$_1$ (ML$_{1A}$) | 56.8% |

INHIBITORS OF PAXILLIN FUNCTION AND RELATED COMPOSITIONS AND METHODS

RELATED APPLICATIONS

This application is a 35 U.S.C. §371 filing of International Application No. PCT/US2015/014473, filed Feb. 4, 2015, which claims priority to U.S. Provisional Application No. 61/935,616, filed Feb. 4, 2014, the entire contents of which are incorporated herein by reference in their entireties for all purposes.

TECHNICAL FIELD

This disclosure relates to small molecule inhibitors of paxillin function and related compositions and methods of treatment.

BACKGROUND

In 2010, the World Health Organization estimated that 39 million people worldwide face blindness; approximately 10% as a result of age-related macular degeneration (AMD) and diabetic retinopathy (DR). The incidence of DR and AMD is increasing as the population ages and the diabetic epidemic spreads throughout the developing world. Moreover, new diagnosis of both non-proliferative and proliferative DR is associated with an increase in wet (exudative/neovascular) AMD. As recent as 2012, approximately 93 million people suffer from DR; over 70% of which endure vision-threatening complications stemming from an exudative retina. Intravitreal injection of anti-VEGF protein therapeutics is most often used to treat AMD and DR, despite the fact that a significant number of patients are refractory. In addition, there is evidence that early efficacy of anti-VEGF interventions may be lost after long-term (i.e, >2 years) exposure. Mounting evidence supports a role for endogenous VEGF in maintenance of visual function through protection of the choriocapillaris and the neural retina. Together, these data suggest that long-term use of anti-VEGF protein therapeutics may contribute to visual impairment by removing an essential support mechanism for the neural retina.

Paxillin is a phosphotyrosine-containing protein in cells that serves as a docking protein, recruiting signaling molecules to a specific cellular compartment, the focal adhesions, and recruiting specific combinations of signaling molecules into a complex to coordinate downstream signaling. Paxillin-coordinated signaling plays a role in the regulation of cell migration, motility and survival. There is a need for compounds that effectively inhibit paxillin function. Accordingly, the present invention describes compounds according to Formulas (I), (Ia), (II), (III), and (IV), as inhibitors of paxillin, and a companion ocular microemulsion (ME) delivery system.

SUMMARY

In one aspect, provided herein is a compound having the structure of Formula (I):

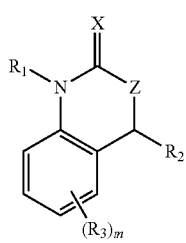

(I)

or a pharmaceutically acceptable salt thereof, wherein:
X is O or S;
Z is O or NH;
$R_1$ is selected from the group consisting of hydrogen, alkyl and arylalkyl;
$R_2$ is aryl, wherein the aryl group is optionally substituted one or more times with a substituent selected from the group consisting of halogen and alkoxy;
$R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; or wherein any two adjacent $R_3$ groups may combine to form a fused aromatic ring, wherein said fused aromatic ring can be substituted one or more times with $R_4$;
$R_4$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; and
m is 0, 1, 2, 3 or 4.

In one embodiment, the compound of Formula (I) has the structure of Formula (II):

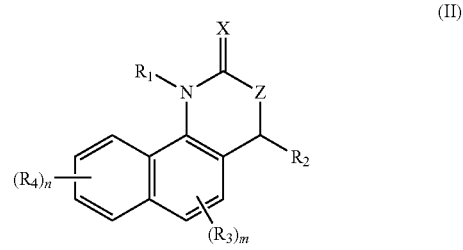

(II)

or a pharmaceutically acceptable salt thereof, wherein: $R_3$ and $R_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; m is 0, 1 or 2; and n is 0, 1, 2, 3 or 4.

In another aspect, provided herein is a compound having the structure of Formula

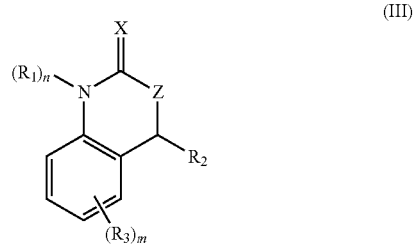

(III)

or a pharmaceutically acceptable salt thereof, wherein:
X is O or S;
Z is selected from O, NH, or $CH_2$;
A is N or O;
$R_1$ is selected from the group consisting of hydrogen, alkyl and arylalkyl;
$R_2$ is aryl, wherein the aryl group is optionally substituted one or more times with a substituent selected from the group consisting of halogen, hydroxy and alkoxy;
$R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; or wherein any two adjacent $R_3$ may combine to form a fused aromatic or heteroaromatic ring, wherein said fused aromatic or heteroaromatic ring can be substituted one or more times with $R_4$;

$R_4$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido;

m is 0, 1, 2, 3 or 4; and n is 0 or 1.

In one embodiment, the compound of Formula (III) has the structure of Formula (IV):

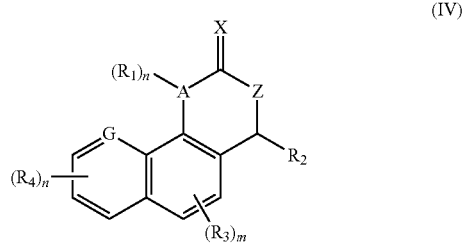

(IV)

or a pharmaceutically acceptable salt thereof, wherein:

G is CH or N;

$R_3$ and $R_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido;

m is 0, 1 or 2;

n is 0 or 1; and p is 0, 1, 2, 3 or 4.

In another aspect, provided herein is a pharmaceutical composition comprising a compound of Formula (I), Formula (II), Formula (III), or Formula (IV), or a pharmaceutically acceptable salt thereof, and a pharmaceutically acceptable carrier.

In still another aspect, provided herein is a method for the treatment of a disorder selected from the group consisting of cancer, metastatic cancer, retinal neovascularization, radiation retinopathy, diabetic retinopathy and polycystic kidney disease in a mammal, comprising administering to the mammal an effective amount of i) a compound of Formula (I), Formula (II), Formula (III), or Formula (IV), or a pharmaceutically acceptable salt thereof, or ii) a pharmaceutical composition comprising a compound of Formula (I), Formula (II), Formula (III), or Formula (IV), or a pharmaceutically acceptable salt thereof, and a pharmaceutically acceptable carrier.

BRIEF DESCRIPTION OF THE DRAWINGS

FIG. 7 shows microsomal stability of compound (II-4).

FIG. 8 shows cytochrome P-450 interaction studies using human microsomes.

FIG. 9 shows the increased susceptibility of primary uveal melanoma (UM) cell lines to apoptosis versus metastatic UM.

FIG. 10 is a table showing 8 genes with high fold expression in metastatic UM relative to primary UM. Assay included a cohort of 84 genes associated with adhesion, invasion and metastasis.

FIG. 11 is a table showing 22 genes with high fold expression in primary UM relative to metastatic UM.

FIG. 12 shows protein levels of a cohort of adhesion molecules in primary and metastatic UM: panel A shows increased VLA-4 protein levels by primary UM (Mel 270) cell line compared to its metastatic counterpart (OMM 2.5); panel B shows the quantitation of all experiments (from FIG. 12, panel A)+/−SD; panel C shows that VLA-4 protein levels are similar in metastatic UM (OMM 2.1) and primary UM (92.1) that does not metastasize; and panel D shows the quantitation of all experiments (from FIG. 12, panel C)+/−SD.

FIG. 14 shows that metastatic UM cells express reduced levels of pY118 upon treatment with compound (II-4): panel A shows a representative Western Blot; and panel B shows quantitation of FIG. 14, panel A.

FIG. 16 present data showing that paxillin inhibition reduced pAKT signaling in metastatic UM cells: panel A shows a representative Western Blot of total and phosphorylated paxillin in metastatic UM cells; panel B shows quantitation of FIG. 16, panel A; panel C shows lysates of metastatic OMM 2.5 cells HGF stimulated in presence or absence of paxillin inhibitor measured by Western Blot; and panel D shows quantitation of FIG. 16, panel C.

FIG. 17, panel A, shows that compound (II-4) inhibits VEGF-induced migration in a scratch wound assay, and panel B shows that there is a significant decrease in migration of RECs following 24 hours of VEGF+ compound (II-4) stimulation.

FIG. 18, panel A, shows that compound (II-4) significantly reduces VEGF-induced cellular proliferation using the WST-1 metabolic assay, and panel B shows that compound (II-4) appears to be non-toxic to retinal endothelial cells after 24 hour incubation.

FIG. 23 shows that compound (II-4) was rapidly metabolized by mouse, rat, ad human cytochrome P-450 enzymes.

FIG. 24 shows that compound (II-4) lacks significant inhibition of cytochrome P-450 family members; the most clinically relevant members 3A4 and 2D6 in particular.

FIG. 25 shows two potential off-target binding candidates.

DETAILED DESCRIPTION

Polycystic Kidney Disease

Figure 1A:
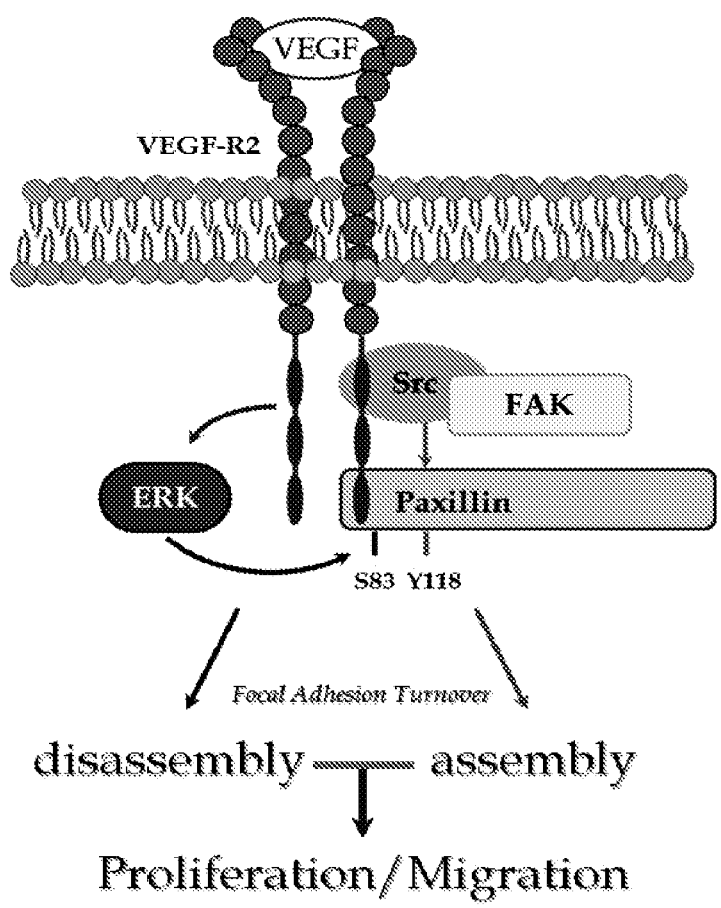
FIG. 1A is a schematic showing signaling events that drive focal adhesion (FA) turnover, and thus angiogenesis, in VEGF-induced RNV.

Polycystic Kidney Disease (PKD) is the most common genetic disease affecting the kidney, and is uniformly characterized by the development of numerous fluid-filled cysts in the kidneys. Cyst growth leads to a loss of functional nephrons in the kidney resulting in end stage renal disease (ESRD). The vast majority of patients with PKD (incidence 1:400-1:1,000) inherit the autosomal dominant form of the disease (ADPKD; MIM 173900; 173910) due to mutation in one of two genes, PKD1 on chromosome 16 or PKD2 on chromosome 4.

The clinical presentation of ADPKD is highly variable, and the genetic mutations in either polycystin-1 (PC-1) or polycystin-2 (PC2) promote a diverse array of abnormal signaling cascades resulting in remodeling of the renal epithelia attributed to epithelial cell proliferation, impaired cell-matrix and cell-cell interaction, and hypersecretion of fluids into the developing cysts.

The claimed method of treating PKD is related to the importance of dysfunctional focal adhesion (FA) attributed to the loss of PC-1 protein in the kidney. It is well established that the focal adhesion complex in the renal epithelial cell plays a critical role in the regulation of adhesion by the cell to the extracellular matrix (ECM), migration, differentiation, and proliferation. The focal adhesion complex is highly dynamic, and is a site in which many signaling and structural proteins are recruited to co-ordinate an organized assembly and disassembly of attachment sites between the cell-matrix and cell-cell. Some of the proteins found at the focal adhesion complex, includes PC-1, other structural proteins (eg. talin, tensin, vinculin, and α-actinin), and signaling proteins (e.g., focal adhesion kinase (FAK) and paxillin). Insufficiency of the focal adhesion-associated proteins tensin, PC-1, and nephrocystin-1 are associated with renal cystic malformation in mice, leading to embryonic lethality in part due to reduced cellular migration.

Without wishing to be bound by theory, it is believed that compounds of the invention (i.e., compounds of Formulas (I), (Ia), (II), (III), and (IV)) block cystic disease progression by restoring focal adhesion function, which is one of the biological parameters perturbed in PKD.

Focal adhesion kinase (FAK) is known to be a critical component at cellular "traction points" known as focal adhesions. FAK is known to phosphorylate multiple substrates, including paxillin, which is an adaptor protein that is associated with focal adhesion assembly and whose phosphorylation at tyrosine 31 and 118 are negatively regulated by mechanical forces. Moreover, PC-1 promotes adhesion and migration of renal epithelial cells by recruiting focal adhesion kinase (FAK) to cellular "traction points" known as focal adhesions (FAs). The C-terminus of PC-1 appears critical to FAK recruitment since FA protein complexes formed in ADPKD epithelial cells always lack FAK. FAK directs FA disassembly while its binding partner, paxillin, promotes assembly and disassembly. Together, they coordinate FA turnover rate. FAK-less FA protein complexes dominated by paxillin lead to altered FA turnover and cystogenesis. Thus, paxillin acts as a "rheostat" that can be targeted to curtail cystogenesis.

Focal adhesions (FAs) facilitate proliferation and migration by bridging both extracellular matrix and growth factor signals to the cytoskeletal machinery. FAK is recruited to nascent FAs where it undergoes autophosphorylation and subsequently activates paxillin, an adaptor protein, at numerous sites, including tyrosines 31 and 118. Among its many functions, the FA-paxillin complex can act as a scaffold for a multitude of other signaling proteins (e.g., talin, vinculin, etc.) and coordinate FA turnover (FIG. 1B). FA turnover is impaired in PKD. In the absence of the cytoplasmic tail (CT) of PC-1, FAs are formed without FAK which leads to reduced FA disassembly and motility. Paxillin has been identified as a key player in radiation-induced angiogenesis within retinal endothelial cells (RECs). Compound (II-4) has been found to prevent vascular endothelial growth factor (VEGF) mediated REC migration (FIG. 2) and inhibit phosphorylation at Y118 (FIG. 13B). Since abnormal FA turnover has been shown in the pathogenesis of PKD [due to loss of the PC-1 cytoplasmic tail] and ERK-dependent hyperproliferation.

Figure 3:
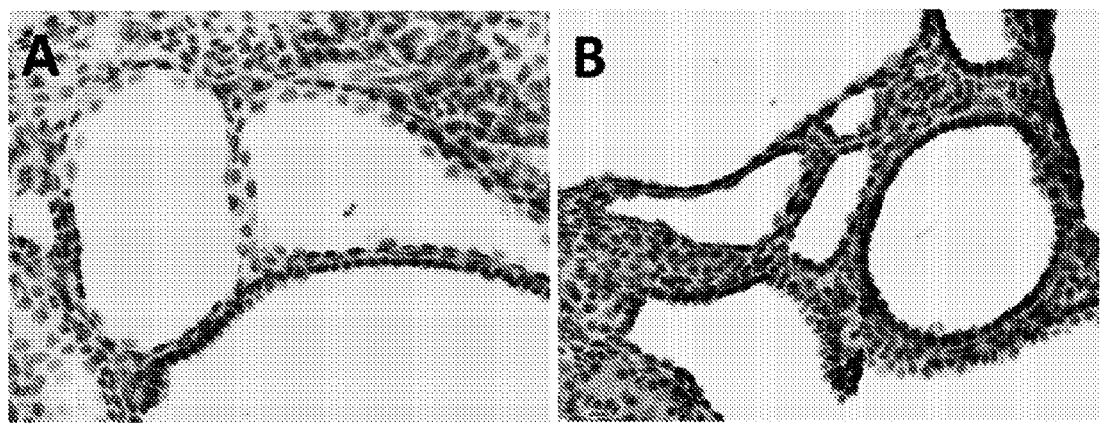
FIG. 3 shows results (at a magnification of 40×) of an immunohistochemical analysis of paxillin in autosomal dominant polycystic kidney disease (ADPKD) mouse kidneys: panel A shows that no staining was observed in the negative control section; and panel B shows darker labeling indicative of localization in the cystic epithelial cells as determined by DAB staining.
Figure 4:
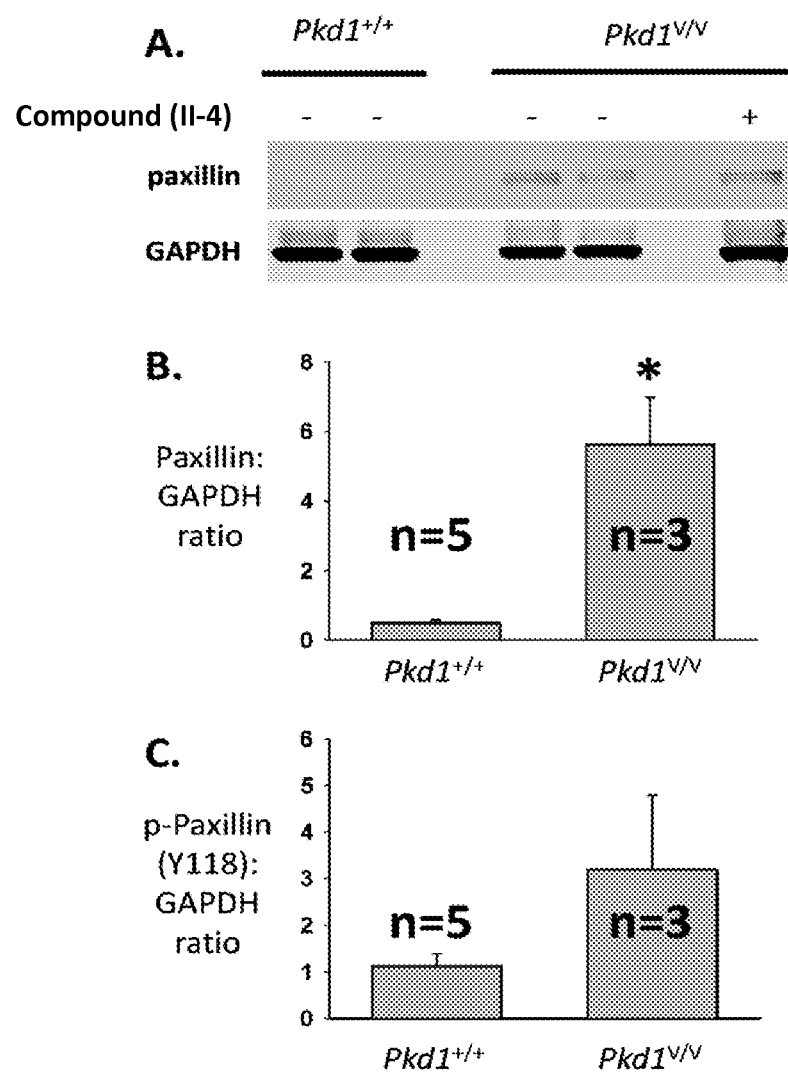
FIG. 4 depicts the presence of paxillin in ADPKD kidneys: panel A shows an immunoblot of total paxillin in protein lysates from non-cystic Pkd1$^{+/+}$ (n=5) and cystic Pkd1$^{V/V}$ (n=3) mouse kidneys at post-natal day 11 after 8 days of dermal application of compound (II-4) microemulsion solution using GAPDH as a loading control; panel B shows the densitometry of the paxillin band normalized to GAPDH where * refers to P<0.005 difference between groups; and panel C shows the densitometry of the phosphor-paxillin band normalized to GAPDH where * refers to P<0.005 difference between groups.

Paxillin is abnormally expressed in cystic epithelial cells in a mouse model of ADPKD. Paxillin expression is markedly increased in cystic ADPKD compared to non-cystic kidneys, and localized to the cystic epithelia (FIGS. 3 and 4).

Figure 5:
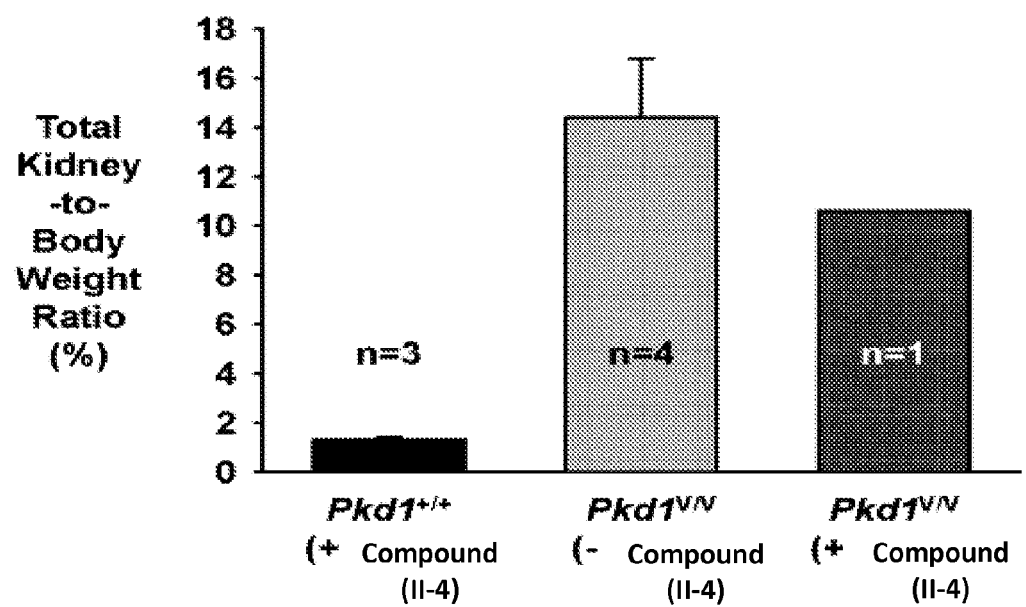
FIG. 5 shows reduction in cyst progression after treatment with paxillin inhibitor compound (II-4).

Long-term dermal application of compound (II-4) reduces paxillin activation in retinal endothelial cells, demonstrated a functional reduction in cystic disease progression in the Pkd1 V/V mouse (FIG. 5). For this reason, paxillin can be considered to act as a "rheostat" that can be targeted to curtail cystogenesis.

The paxillin inhibitor compound (II-4) inactivates phosphorylation at Y118 on paxillin using retinal endothelial cells. Compound (II-4) has been formulated as a microemulsion for non-invasive delivery to neonatal Pkd1 non-cystic and cystic mice and it has been observed that renal cystic disease was attenuated as measured by total kidney-to-body weight ratio.

Immunomodulation of the Alpha-4-Paxillin (α4-Paxillin) Signaling to Enhance Anti-Metastatic Activity in Metastatic Uveal Melanoma Metastasis is the most crucial factor in the survival of cancer patients. About 50% of uveal melanoma (UM) patients are considered high-risk patients and will develop metastasis (<85% in liver) within 5-years after diagnosis of the primary tumor. Although UM comprises 5% of all melanoma cases it is the most common primary intraocular malignancy in adults. Despite 40 years of research in the UM field, there is a lack of understanding what induces the transformation of the uveal melanocytes and hematogenous spread to the liver. There is no effective therapy against the metastatic form of the disease emphasizing the urgency for continuous research in the field. While the primary tumor can be successfully treated with brachytherapy or removal of the eye, at present there is no effective therapy for the treatment of metastatic UM. Advances in molecular genomics have identified several factors associated with prognosis. Initial studies showed evidence that monosomy 3 was associated with increased risk of metastasis. Subsequently, trisomy 8 was suggested to be involved in accelerated metastatic disease due to overexpression of C-MYC genes. Gene Expression Profiling (GEP) analysis divided UM into 2 discrete prognostic classes based upon clustering of upregulated and downregulated genes. GEP highlighted potential differences in the tumor microenvironment, in inflammation-related pathways and dampening of the immune response. Subsequent studies found mutations in inflammation-associated genes like GNAQ and GNA11, suggesting alterations in key signaling pathways such as the MAP kinase signaling cascade.

Although little is known about how UM spread beyond the eye, it has been suggested that (1) enucleation might accelerate tumor spread by dissemination of UM cells into the circulation and (2) eye/tumor removal reduced anti-tumor immune responses. Micro-metastatic disease may be present in the liver at the time of initial diagnosis of primary UM and possibly present for two years prior diagnosis. These results were confirmed through histological examination of metastatic UM. Additional research has focused on invasion properties of UM and identified high levels of c-Met protein in metastatic UM. Another molecule involved in UM tumor dissemination is CXCR4. It has been shown that blocking of CXCR4 by siRNA inhibited the migratory and the invasiveness of UM when exposed to different factors present in the tumor microenvironment. The findings suggest the study of UM requires an understanding of the interplay between the tumor and the microenvironment.

Gene transcription analysis has identified different components downstream of the Src pathway associated with the actin cytoskeleton that may be regulated differently in primary versus metastatic UM. The alpha-4 (α4) integrin subunit that interacts with the cytoskeletal adaptor paxillin has been identified, which controls UM proliferation and migration in vitro. Herein, it is disclosed that blockade of the α4-paxillin signaling using an inhibitor of paxillin, which reduced tyrosine 118 phosphorylation (pY118), disrupts downstream events necessary for the proliferation and migration of cells that become metastases.

Compounds of the Invention

In one aspect, provided herein is a compound having the structure of Formula (I):

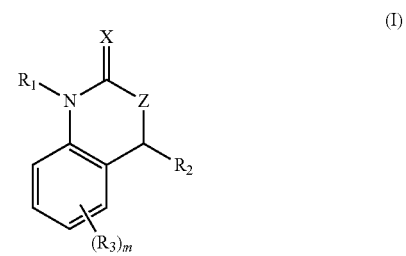

or a pharmaceutically acceptable salt thereof, wherein:

X is O or S;

Z is O or NH;

$R_1$ is selected from the group consisting of hydrogen, alkyl and arylalkyl;

$R_2$ is aryl, wherein the aryl group is optionally substituted one or more times with a substituent selected from the group consisting of halogen and alkoxy;

$R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; or wherein any two adjacent $R_3$ groups may combine to form a fused aromatic ring, wherein said fused aromatic ring can be substituted one or more times with $R_4$;

$R_4$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; and m is 0, 1, 2, 3 or 4.

Provided herein is an embodiment of the compound of Formula (I), wherein $R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido.

In one embodiment, the compound of Formula (I) is selected from the group consisting of:

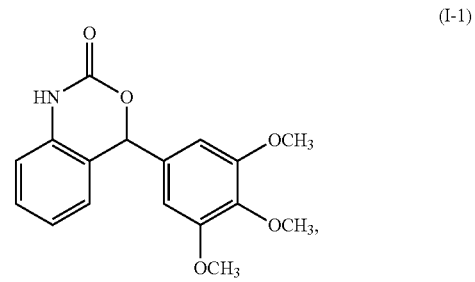 [SMILES: COc1cc(C2OC(=O)Nc3ccccc32)cc(OC)c1OC]

-continued

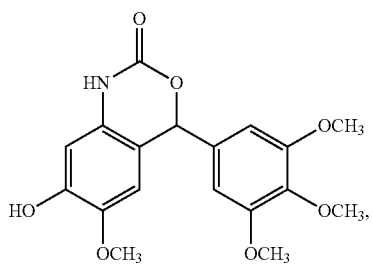
(I-2)

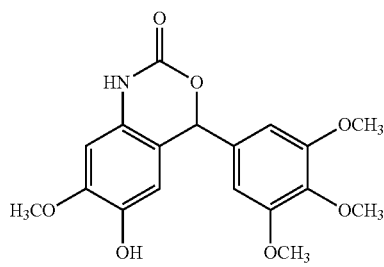
(I-3)

or pharmaceutically acceptable salts thereof.

In another embodiment, the compound of Formula (I) is selected from the group consisting of:

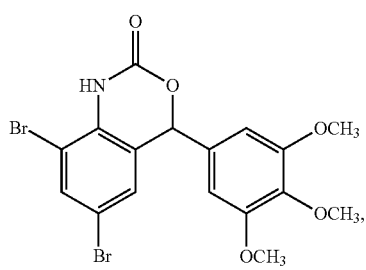
(I-4)

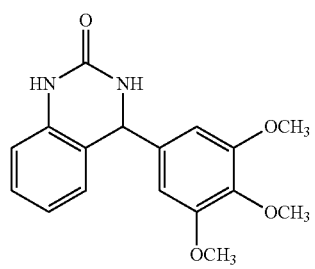
(I-5)

or pharmaceutically acceptable salts thereof.

In a particular embodiment, the compound of Formula (I) is:

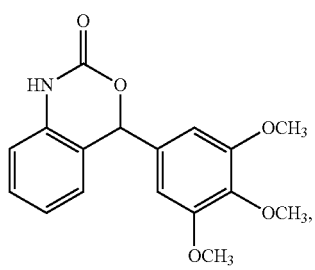
(I-1)

or a pharmaceutically acceptable salt thereof.

In another embodiment, the compound of Formula (I) has the structure of Formula (Ia):

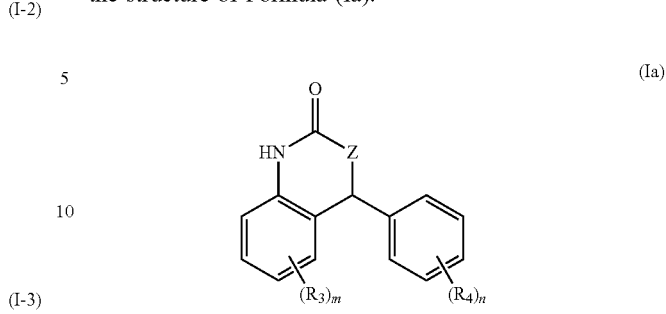
(Ia)

or a pharmaceutically acceptable salt thereof, wherein:
Z is O or NH;
$R_3$, independently for each occurrence, is selected from the group consisting of alkyl, alkenyl, alkoxy, hydroxy, and halogen;
$R_4$, independently for each occurrence, is selected from the group consisting of halogen and alkoxy;
m is 0, 1, or 2; and
n is 0, 1, 2, or 3.

In another embodiment, the compound of Formula (I) has the structure of Formula (II):

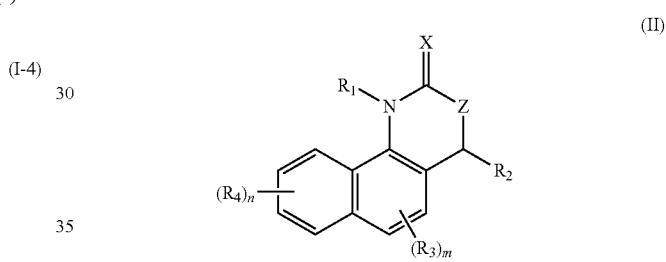
(II)

or a pharmaceutically acceptable salt thereof, wherein: $R_3$ and $R_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; m is 0, 1 or 2; and n is 0, 1, 2, 3 or 4.

In another embodiment of the compound of Formula (II), $R_1$ is hydrogen; $R_2$ is aryl, wherein the aryl group is optionally substituted one or more times with a substituent selected from the group consisting of halogen and alkoxy; $R_3$, independently for each occurrence, is selected from the group consisting of alkoxy and hydroxy; and m is 0, 1 or 2.

In another embodiment of the compound of Formula (II), $R_3$, independently for each occurrence, is selected from the group consisting of alkoxy and halide; and $R_4$ is hydrogen.

In another embodiment, the compound of Formula (II) is selected from the group consisting of:

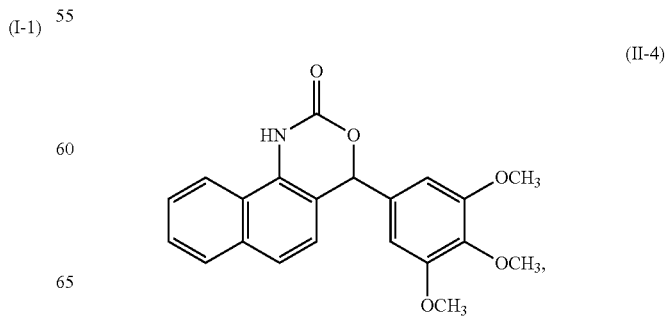
(II-4)

(II-5)

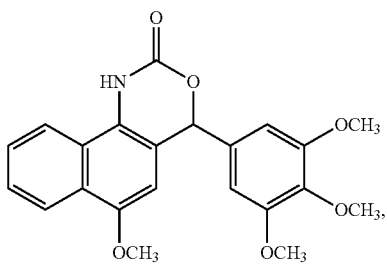

(II-6)

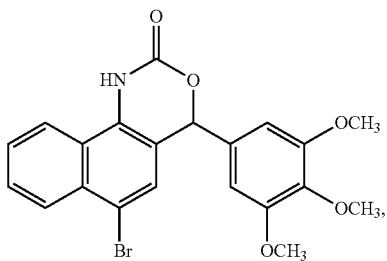

or pharmaceutically acceptable salts thereof.

In another embodiment, the compound of Formula (II) is selected from the group consisting of:

(II-7)

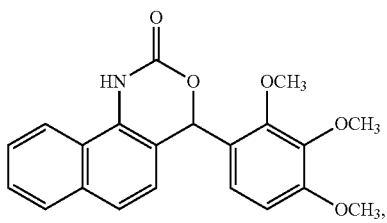

(II-8)

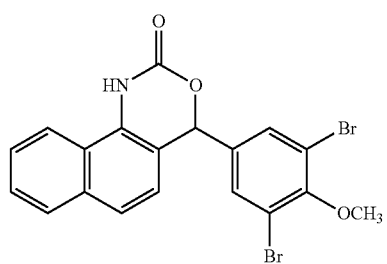

or pharmaceutically acceptable salts thereof.

In a particular embodiment, the compound of Formula (II) is:

(II-4)

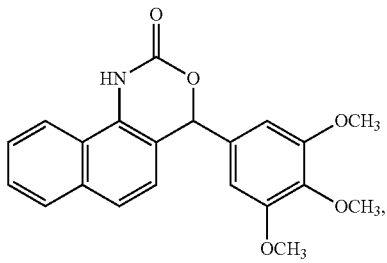

or a pharmaceutically acceptable salt thereof.

In a further particular embodiment, the compound of Formula (II) is:

(II-7)

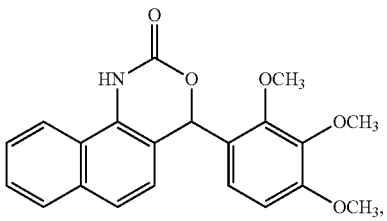

or a pharmaceutically acceptable salt thereof.

Also provided herein are the following alternative embodiments of the compounds of Formulas (I) and (II), wherein:
$R_1$ is hydrogen;
$R_2$ is selected from the group consisting of phenyl, methoxyphenyl, trimethoxyphenyl, bromomethoxyphenyl and dibromomethoxyphenyl;
$R_2$ is 3,4,5-trimethoxyphenyl;
X is O;
X is S;
Z is O;
Z is NH;
X is O and Z is O;
X is O and Z is NH;
X is S and Z is O;
X is S and Z is NH;
the compound has (R) stereochemistry (e.g., 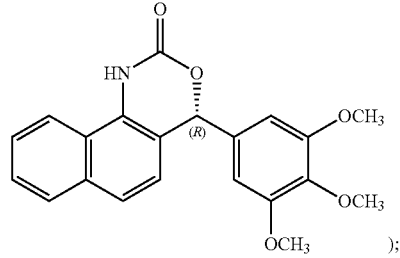 );

or
the compound has (S) stereochemistry (e.g., 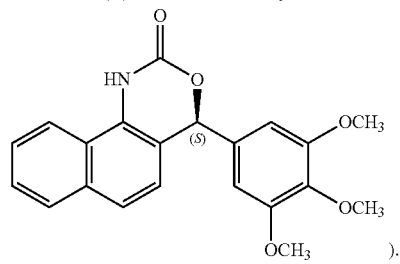 ).

In another aspect, provided herein is a compound having the structure of Formula (III):

(III)

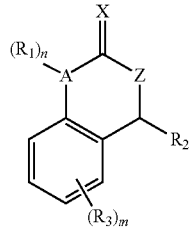

or a pharmaceutically acceptable salt thereof, wherein:
X is O or S;
Z is selected from O, NH, or $CH_2$;

A is N or O;

$R_1$ is selected from the group consisting of hydrogen, alkyl and arylalkyl;

$R_2$ is aryl, wherein the aryl group is optionally substituted one or more times with a substituent selected from the group consisting of halogen, hydroxy and alkoxy;

$R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; or wherein any two adjacent $R_3$ may combine to form a fused aromatic or heteroaromatic ring, wherein said fused aromatic or heteroaromatic ring can be substituted one or more times with $R_4$;

$R_4$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido;

m is 0, 1, 2, 3 or 4; and n is 0 or 1.

In one embodiment, when A is O, n is 0.

In another embodiment, when A is N, $R_1$ is H.

In another embodiment, m is 0, 1, 2, or 3.

In another embodiment, m is 0.

In another embodiment, $R_4$, independently for each occurrence, is selected from the group consisting of alkyl, alkenyl, alkoxy, hydroxy, and halogen. In a particular embodiment, $R_4$, independently for each occurrence, is selected from the group consisting of alkoxy, hydroxy, and halogen.

In another embodiment, $R_2$ is aryl, wherein the aryl group is optionally substituted one or more times with a substituent selected from the group consisting of hydroxy and alkoxy.

In another embodiment, $R_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido.

In another embodiment, $R_3$, independently for each occurrence, is selected from the group consisting of alkyl, alkenyl, alkoxy, hydroxy, and halogen. In a particular embodiment, $R_3$, independently for each occurrence, is selected from the group consisting of alkoxy, hydroxy, and halogen.

In one embodiment, the compound of Formula (III) is selected from the group consisting of:

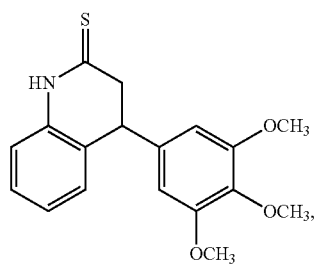

(III-1)

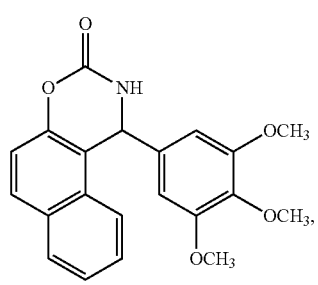

(III-2)

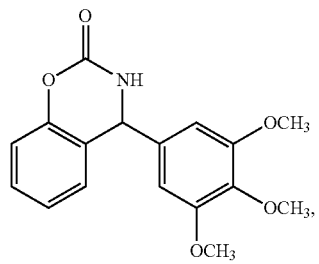

(III-3)

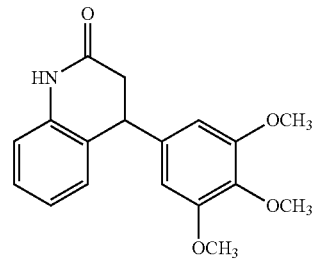

(III-4)

or pharmaceutically acceptable salts thereof.

In another embodiment, the compound of Formula (III) has the structure of Formula (IV):

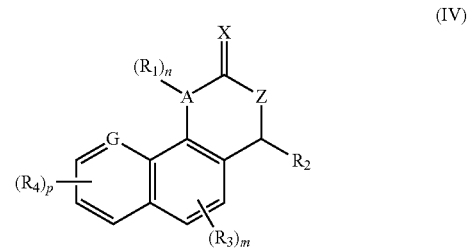

(IV)

or a pharmaceutically acceptable salt thereof, wherein:

G is CH or N;

$R_3$ and $R_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido;

m is 0, 1 or 2;

n is 0 or 1; and p is 0, 1, 2, 3 or 4.

In one embodiment, p is 0, 1, or 2.

In one embodiment, when A is O, n is 0.

In another embodiment, when A is N, $R_1$ is H.

In another embodiment, p is 0, 1, or 2.

In another embodiment, p and m are 0.

In another embodiment, $R_3$ and $R_4$, independently for each occurrence, are selected from the group consisting of alkyl, alkenyl, alkoxy, hydroxy, and halogen. In a particular embodiment, $R_3$ and $R_4$, independently for each occurrence, are selected from the group consisting of alkoxy, hydroxy, and halogen.

In another embodiment, $R_2$ is aryl, wherein the aryl group is optionally substituted one or more times with a substituent selected from the group consisting of hydroxy and alkoxy.

In another embodiment, the compound of Formula (IV) is selected from the group consisting of:

(IV-1)
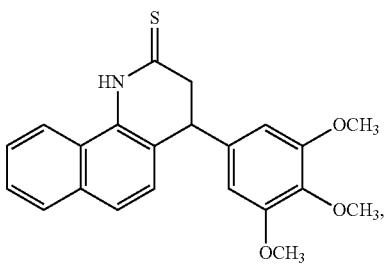

(IV-2)
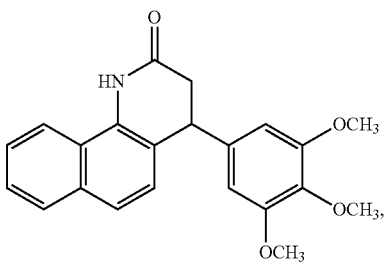

(IV-3)
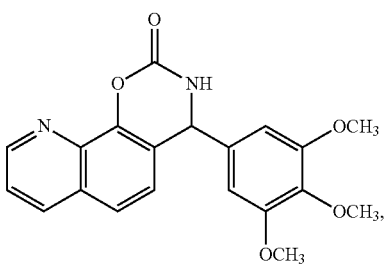

(IV-4)
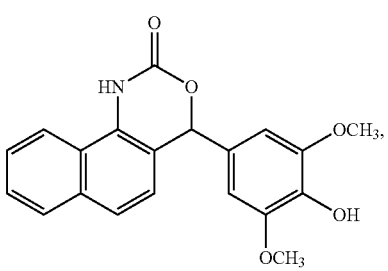

(IV-5)
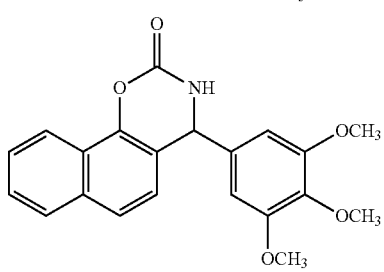

or pharmaceutically acceptable salts thereof.

In another embodiment, the compound of Formula (IV) is selected from the group consisting of:

(IV-2)
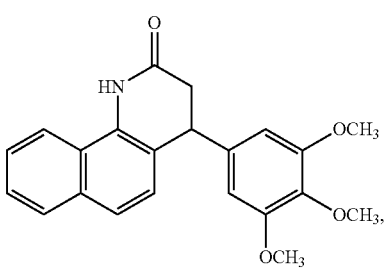

(IV-4)
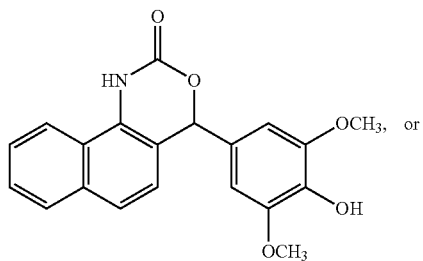

(IV-5)
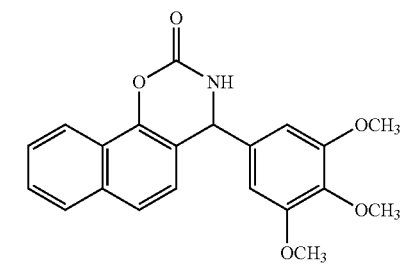

or a pharmaceutically acceptable salt thereof.

Also provided herein are the following alternative embodiments of the compounds of Formulas (III) and (IV), wherein:

$R_1$ is hydrogen;

$R_2$ is selected from the group consisting of phenyl, methoxyphenyl, trimethoxyphenyl, bromomethoxyphenyl and dibromomethoxyphenyl;

$R_2$ is 3,4,5-trimethoxyphenyl;

X is O;

X is S;

Z is O;

Z is NH;

Z is $CH_2$;

A is N;

A is O;

X is O and Z is O;

X is O and Z is NH;

X is S and Z is O;

X is S and Z is NH;

the compound has (R) stereochemistry (e.g., 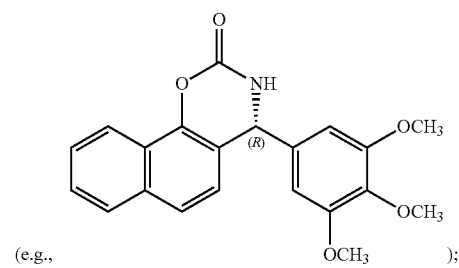 );

or
the compound has (S) stereochemistry (e.g., 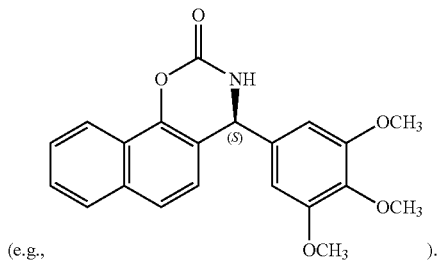 ).

Definitions

As used herein, the term "compound" is intended to mean a substance made up of molecules that further consist of atoms. A compound may be any natural or non-natural material, for example, peptide or polypeptide sequences, organic or inorganic molecules or compositions, nucleic acid molecules, carbohydrates, lipids or combinations thereof. A compound generally refers to a chemical entity, whether in the solid, liquid or gaseous phase, and whether in a crude mixture or purified and isolated. Compounds encompass the chemical compound itself as well as, where applicable: amorphous and crystalline forms of the compound, including polymorphic forms, said forms in mixture or in isolation; free acid and free base forms of the compound; isomers of the compound, including geometric isomers, optical isomers, and tautomeric isomers, said optical isomers to include enantiomers and diastereomers, chiral isomers and non-chiral isomers, said optical isomers to include isolated optical isomers or mixtures of optical isomers including racemic and non-racemic mixtures; said geometric isomers to include transoid and cisoid forms, where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, including acid addition salts and base addition salts, including organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different.

As used herein, "alkyl" groups include saturated hydrocarbons having one or more carbon atoms, including straight-chain alkyl groups (e.g., methyl, ethyl, propyl, butyl, pentyl, hexyl, etc.), cyclic alkyl groups (or "cycloalkyl" or "alicyclic" or "carbocyclic" groups) (e.g., cyclopropyl, cyclopentyl, cyclohexyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). In certain embodiments, a straight-chain or branched-chain alkyl group may have 8 or fewer carbon atoms in its backbone, e.g., $C_1$-$C_8$ for straight-chain or $C_3$-$C_8$ for branched-chain. In certain embodiments, a straight-chain or branched-chain alkyl group may have 6 or fewer carbon atoms in its backbone, e.g., $C_1$-$C_6$ for straight-chain or $C_3$-$C_6$ for branched-chain. In still other embodiments, an alkyl group includes about 1 to 4 carbons. In other embodiments, an alkyl group includes about 1 to 3 carbons. In yet other embodiments, an alkyl group includes about 1 or 2 carbons. The term "lower alkyl" refers to alkyl groups having from 1 to 6 carbons in the chain, and to cycloalkyl groups having from 3 to 6 carbons in the ring structure. The term "$C_1$-$C_6$" as in "$C_1$-$C_6$ alkyl" means alkyl groups containing 1 to 6 carbon atoms. The terms "alkenyl" and "alkynyl" refer to unsaturated aliphatic groups analogous to alkyls, but which contain at least one double or triple carbon-carbon bond respectively.

The term "alkoxy" as used herein means an alkyl group having an oxygen atom attached thereto. In some embodiments, alkoxy groups include groups having 1 to about 8 carbon atoms. In other embodiments, alkoxy groups include groups having 1 to about 6 carbon atoms. In still other embodiments, alkoxy groups include groups having fewer than about 4 carbon atoms. Examples of alkoxy groups include, but are not limited to, methoxy, ethoxy, isopropyloxy, propoxy, butoxy, and pentoxy groups. The alkoxy groups can be straight-chain or branched.

The term "amine" or "amino," as used herein, refers to an unsubstituted or substituted moiety of the formula —$NR^aR^b$, in which $R^a$ and $R^b$ are each independently hydrogen, alkyl, or aryl. Thus, the term amino includes alkylamino (e.g., $R^a$ is hydrogen and $R^b$ is alkyl) and dialkylamino (e.g., $R^a$ is alkyl and $R^b$ is alkyl). Alternatively, $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated.

The terms "amide" or "amido" refers to a substituent group —C(O)—$NR^aR^b$, wherein $R^a$ and $R^b$ are defined as above, and wherein the point of connectivity of the substituent is the carbonyl carbon. Thus, the term amido includes alkylamido (e.g., $R^a$ is hydrogen and $R^b$ is alkyl), dialkylamido (e.g., $R^a$ is alkyl and $R^b$ is alkyl) and arylamido (e.g., $R^a$ is hydrogen and $R^b$ is aryl). Alternatively, $R^a$ and $R^b$, taken together with the nitrogen atom to which they are attached, form a cyclic moiety having from 3 to 8 atoms in the ring.

The terms "aryl" and "aryl group" include unsaturated and aromatic cyclic hydrocarbons as well as unsaturated and aromatic heterocycles containing one or more rings. Aryl groups include, for example $C_{5-8}$ aryl groups. Aryl groups may also be fused or bridged with alicyclic or heterocyclic rings that are not aromatic so as to form a polycycle (e.g., tetralin).

Regarding connectivity, an "arylalkyl" group, for example, is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)).

"Treatment", "to treat" or "treating" as used herein, is defined as the application or administration of a therapeutic agent (e.g., a compound of the invention) to a patient, or to an isolated tissue or cell line from a patient. The patient generally has a disease or disorder, a symptom of disease or disorder or a predisposition toward a disease or disorder. The purpose of treatment is generally to cure, heal, alleviate, relieve, remedy, ameliorate, or improve such disease, disorder, symptoms or predisposition. "Treated," as used herein, refers to the disease or disorder being cured, healed, alleviated, relieved, remedied, ameliorated, or improved. For example, methods of treatment of the instant invention provide for administration of an inhibitor as described herein, such that the progression of a specific disorder is slowed or stopped. Methods of treatment of the instant invention further include the administration of an inhibitor, such that a specific disorder is cured.

The term "effective amount" is defined as an amount sufficient to achieve a desired effect. The term "desired effect" refers generally to any result that is anticipated by the skilled artisan when a compound or composition of the invention is administered to a subject. In some embodiments, the desired effect is a complete remission of the disease or disorder. In other embodiments, the desired effect is a partial treatment of a disease or disorder. In still other embodiments, the desired effect is a full or partial treatment of the symptoms of a disease or disorder.

Pharmaceutical Compositions

In another aspect, provided herein is a pharmaceutical composition comprising a compound of Formula (I), Formula (Ia), Formula (II), Formula (III), or Formula (IV), or a pharmaceutically acceptable salt thereof, and a pharmaceutically acceptable carrier.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

A compound of Formula (I), Formula (Ia), Formula (II), Formula (III), or Formula (IV) can be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with a compound of Formula (I), Formula (Ia), Formula (II), Formula (III), or Formula (IV), such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Pharmaceutical compositions comprising a compound of Formula (I), Formula (Ia), Formula (II), Formula (III), or Formula (IV) may be formulated to have any concentration desired. In some embodiments, the composition is formulated such that it comprises at least a therapeutically effective amount. In some embodiments, the composition is formulated such that it comprises an amount that would not cause one or more unwanted side effects.

Provided herein is a microemulsion-based delivery system for transdermal delivery. Also provided herein is a nanoemulsion-based delivery system. Drug dosing into small animals, especially mice, is a considerable challenge to biomedical scientists. Intraperitoneal injection is one of the most common methods to deliver therapeutics, but there can be difficulties in determining whether the whole drug dosage has been administered and not leaked out of the animal pup.

In a particular embodiment, provided herein is a pharmaceutical composition comprising a compound of Formula (I), Formula (Ia), Formula (II), Formula (III), or Formula (IV), or a pharmaceutically acceptable salt thereof, wherein the compound is formulated in a microemulsion.

In another particular embodiment, provided herein is a pharmaceutical composition comprising a compound of Formula (I), Formula (Ia), Formula (II), Formula (III), or Formula (IV), or a pharmaceutically acceptable salt thereof, wherein the compound is formulated as an eye-drop.

Methods of Treatment

In one aspect, provided herein is a method for the treatment of a disorder selected from the group consisting of metastatic cancer, retinal neovascularization, radiation retinopathy, diabetic retinopathy and polycystic kidney disease, in a mammal, comprising administering to the mammal an effective amount of a compound of Formula (I), Formula (Ia), Formula (II), Formula (III), or Formula (IV), or a pharmaceutically acceptable salt thereof, or a pharmaceutical composition comprising a compound of Formula (I), Formula (Ia), Formula (II), Formula (III), or Formula (IV), or a pharmaceutically acceptable salt thereof, and a pharmaceutically acceptable carrier. In a particular embodiment, the mammal is a human.

In another aspect, provided herein is a method for the treatment of a disorder selected from the group consisting of cancer, metastatic cancer, retinal neovascularization, radiation retinopathy, diabetic retinopathy and polycystic kidney disease, in a mammal, comprising administering to the mammal an effective amount of a compound of Formula (I), Formula (Ia), Formula (II), Formula (III), or Formula (IV), or a pharmaceutically acceptable salt thereof, or a pharmaceutical composition comprising a compound of Formula (I), Formula (Ia), Formula (II), Formula (III), or Formula (IV), or a pharmaceutically acceptable salt thereof, and a pharmaceutically acceptable carrier. In a particular embodiment, the mammal is a human.

In one embodiment, the polycystic kidney disease is autosomal dominant polycystic kidney disease.

In one embodiment of the method, the retinal neovascularization is due to diabetic retinopathy or radiation retinopathy. The radiation retinopathy may be due to exposure of the mammal's retinal endothelial cells to radiation, wherein, for example, the radiation is used to treat an intraocular tumor. In a non-limiting embodiment, the radiation is gamma radiation (i.e., γ ray).

In one embodiment of the method, the diabetic retinopathy is due to exposure of the mammal's retinal endothelial cells to high glucose levels.

In one embodiment of the method, the treatment of retinal neovascularization promotes or maintains retinal endothelial cell viability. In another embodiment, the treatment of retinal neovascularization reduces retinal endothelial cell death.

In one embodiment, the methods described herein are used in combination with one or more existing treatment methods for radiation retinopathy or diabetic retinopathy.

In one embodiment of the method, the cancer is uveal melanoma. In another embodiment, the metastatic cancer is metastatic uveal melanoma.

In another aspect, provided herein is a method of inhibiting paxillin function in a mammal, comprising administering to the mammal an effective amount of a compound of Formula (I), Formula (Ia), Formula (II), Formula (III), or Formula (IV), or a pharmaceutically acceptable salt thereof, or a pharmaceutical composition comprising a compound of Formula (I), Formula (Ia), Formula (II), Formula (III), or Formula (IV), or a pharmaceutically acceptable salt thereof, and a pharmaceutically acceptable carrier.

Accordingly, in one embodiment, provided herein is a method of treating retinal neovascularization in a subject in need thereof, comprising administering the subject a therapeutically effective amount of a compound of Formula (I), or a pharmaceutically acceptable salt thereof.

Accordingly, in one embodiment, provided herein is a method of treating retinal neovascularization in a subject in need thereof, comprising administering the subject a therapeutically effective amount of compound I-1, or a pharmaceutically acceptable salt thereof.

In another embodiment, provided herein is a method of treating retinal neovascularization in a subject in need thereof, comprising administering the subject a therapeutically effective amount of compound I-2, or a pharmaceutically acceptable salt thereof.

In another embodiment, provided herein is a method of treating retinal neovascularization in a subject in need thereof, comprising administering the subject a therapeutically effective amount of compound I-3, or a pharmaceutically acceptable salt thereof.

In another embodiment, provided herein is a method of treating retinal neovascularization in a subject in need thereof, comprising administering the subject a therapeutically effective amount of compound I-4, or a pharmaceutically acceptable salt thereof.

In another embodiment, provided herein is a method of treating retinal neovascularization in a subject in need thereof, comprising administering the subject a therapeutically effective amount of compound I-5, or a pharmaceutically acceptable salt thereof.

In one embodiment, provided herein is a method of treating retinal neovascularization in a subject in need thereof, comprising administering the subject a therapeutically effective amount of a compound of Formula (II), or a pharmaceutically acceptable salt thereof.

In another embodiment, provided herein is a method of treating retinal neovascularization in a subject in need thereof, comprising administering the subject a therapeutically effective amount of compound II-1, or a pharmaceutically acceptable salt thereof.

In another embodiment, provided herein is a method of treating retinal neovascularization in a subject in need thereof, comprising administering the subject a therapeutically effective amount of compound II-2, or a pharmaceutically acceptable salt thereof.

In another embodiment, provided herein is a method of treating retinal neovascularization in a subject in need thereof, comprising administering the subject a therapeutically effective amount of compound II-3, or a pharmaceutically acceptable salt thereof.

In another embodiment, provided herein is a method of treating retinal neovascularization in a subject in need thereof, comprising administering the subject a therapeutically effective amount of compound II-4, or a pharmaceutically acceptable salt thereof.

In another embodiment, provided herein is a method of treating retinal neovascularization in a subject in need thereof, comprising administering the subject a therapeutically effective amount of compound II-5, or a pharmaceutically acceptable salt thereof.

In another embodiment, provided herein is a method of treating retinal neovascularization in a subject in need thereof, comprising administering the subject a therapeutically effective amount of compound II-6, or a pharmaceutically acceptable salt thereof.

In another embodiment, provided herein is a method of treating retinal neovascularization in a subject in need thereof, comprising administering the subject a therapeutically effective amount of compound II-7, or a pharmaceutically acceptable salt thereof.

In another embodiment, provided herein is a method of treating retinal neovascularization in a subject in need thereof, comprising administering the subject a therapeutically effective amount of compound II-8, or a pharmaceutically acceptable salt thereof.

In one embodiment, provided herein is a method of treating retinal neovascularization in a subject in need thereof, comprising administering the subject a therapeutically effective amount of a compound of Formula (III), or a pharmaceutically acceptable salt thereof.

In another embodiment, provided herein is a method of treating retinal neovascularization in a subject in need thereof, comprising administering the subject a therapeutically effective amount of compound III-1, or a pharmaceutically acceptable salt thereof.

In another embodiment, provided herein is a method of treating retinal neovascularization in a subject in need thereof, comprising administering the subject a therapeutically effective amount of compound III-2, or a pharmaceutically acceptable salt thereof.

In another embodiment, provided herein is a method of treating retinal neovascularization in a subject in need thereof, comprising administering the subject a therapeutically effective amount of compound III-3, or a pharmaceutically acceptable salt thereof.

In another embodiment, provided herein is a method of treating retinal neovascularization in a subject in need thereof, comprising administering the subject a therapeutically effective amount of compound III-4, or a pharmaceutically acceptable salt thereof.

In one embodiment, provided herein is a method of treating retinal neovascularization in a subject in need thereof, comprising administering the subject a therapeutically effective amount of a compound of Formula (IV), or a pharmaceutically acceptable salt thereof.

In another embodiment, provided herein is a method of treating retinal neovascularization in a subject in need thereof, comprising administering the subject a therapeutically effective amount of compound IV-1, or a pharmaceutically acceptable salt thereof.

In another embodiment, provided herein is a method of treating retinal neovascularization in a subject in need thereof, comprising administering the subject a therapeutically effective amount of compound IV-2, or a pharmaceutically acceptable salt thereof.

In another embodiment, provided herein is a method of treating retinal neovascularization in a subject in need thereof, comprising administering the subject a therapeutically effective amount of compound IV-3, or a pharmaceutically acceptable salt thereof.

In another embodiment, provided herein is a method of treating retinal neovascularization in a subject in need thereof, comprising administering the subject a therapeutically effective amount of compound IV-4, or a pharmaceutically acceptable salt thereof.

In another embodiment, provided herein is a method of treating retinal neovascularization in a subject in need thereof, comprising administering the subject a therapeutically effective amount of compound IV-5, or a pharmaceutically acceptable salt thereof.

EXPERIMENTALS

Selected compounds of Formulas (I), (Ia), (II), (III), and (IV), were synthesized according to the general representative procedure for the synthesis of compound (II-4) (Scheme 1).

Scheme 1.

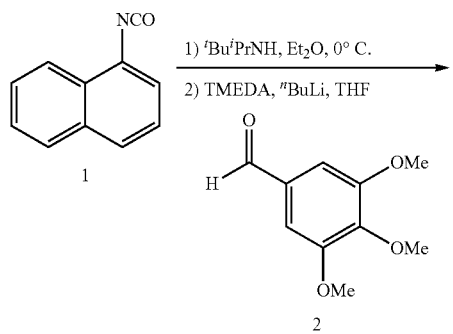

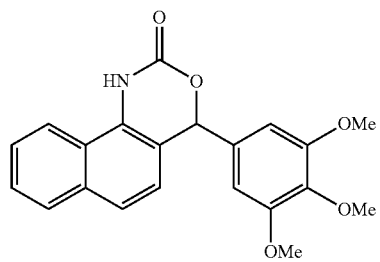

Compound (II-4)

Each compound was characterized with high-resolution mass and nuclear magnetic resonance spectroscopy.

II-4

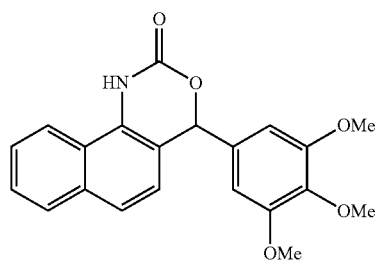

Chemical Formula: $C_{21}H_{19}NO_5$
Exact Mass: 365.13
Molecular Weight: 365.38

Purification by silica gel column chromatography (Hexanes:EtOAc 80:20 to 50:50) gave compound (II-4) (44 mg, 0.064 mmol, 95%) as a white foam. TLC (Hexanes:EtOAc 50:50): $R_f$=0.7; $^1$H NMR (CDCl$_3$, 500 MHz) δ 9.11 (d, J=3.6 Hz, 1H), 8.10 (d, J=5.0 Hz, 1H), 7.88 (d, J=5.1 Hz, 1H), 7.65-7.50 (m, 3H), 7.0 (d, J=6.1 Hz, 1H), 6.63 (s, 2H), 6.50 (s, 1H), 3.85 (s, 3H), 3.75 (s, 6H); HRMS (ESI$^+$): m/z calcd for $C_{21}H_{19}NNaO_5$ [M+Na], 388.116. found 388.118.

I-1

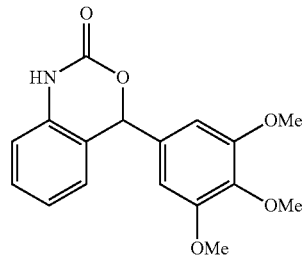

Chemical Formula: $C_{17}H_{17}NO_5$
Exact Mass: 315.11
Molecular Weight: 315.32

Purification by silica gel column chromatography (Hexanes:EtOAc 80:20 to 50:50) gave compound (I-1) as a white solid. TLC (Hexanes:EtOAc 50:50): $R_f$=0.8; $^1$H NMR (CDCl$_3$, 500 MHz) δ 8.76 (s, 1H), 7.31 (m, 1H), 7.03 (m, 1H), 6.94-6.88 (m, 2H), 6.58 (s, 2H), 6.32 (s, 1H), 3.88 (s, 3H), 3.82 (s, 6H); HRMS (ESI$^+$): m/z calcd for $C_{17}H_{17}NNaO_5$ [M+Na], 338.100. found 338.102.

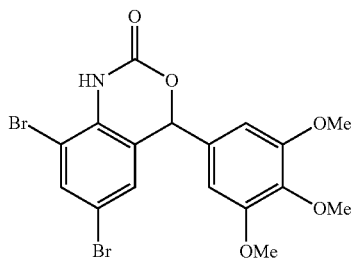

I-4

Chemical Formula: C₁₇H₁₅Br₂NO₅
Exact Mass: 470.93
Molecular Weight: 473.11

Purification by silica gel column chromatography (Hexanes:EtOAc 80:20 to 50:50) gave compound (I-4) as a white solid. TLC (Hexanes:EtOAc 50:50): $R_f$=0.6; ¹H NMR (CDCl₃, 500 MHz) δ 7.85 (s, 1H), 7.44 (d, J=8.5 Hz, 1H), 6.82-6.74 (m, 4H), 3.97 (s, 3H), 3.96 (s, 3H), 3.81 (s, 3H); HRMS (ESI⁺): m/z calcd for C₁₇H₁₅Br₂NNaO₅ [M+Na], 493.921. found 493.922.

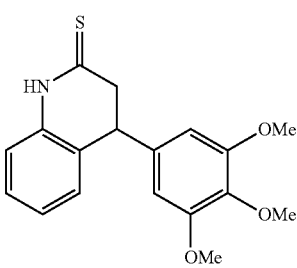

III-1

Chemical Formula: C₁₈H₁₉NO₃S
Exact Mass: 329.11
Molecular Weight: 329.41

Purification by silica gel column chromatography (Hexanes:EtOAc 80:20 to 50:50) gave compound (III-1) as a white solid. TLC (Hexanes:EtOAc 50:50): $R_f$=0.7; ¹H NMR (CDCl₃, 500 MHz) δ 9.96 (s, 1H), 7.27-7.25 (m, 1H), 7.09-7.07 (m, 1H), 7.02 (d, J=8.0 Hz, 1H), 6.93 (d, J=8.0 Hz, 1H), 6.44 (s, 2H), 4.14 (m, 1H), 3.85 (s, 3H), 3.81 (s, 6H), 3.37 (m, 2H); HRMS (ESI⁺): m/z calcd for C₁₈H₁₉NNaO₃S [M+Na], 352.098. found 352.097.

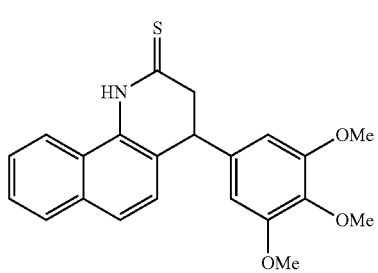

IV-1

Chemical Formula: C₂₂H₂₁NO₃S
Exact Mass: 379.12
Molecular Weight: 379.47

Purification by silica gel column chromatography (Hexanes:EtOAc 80:20 to 50:50) gave compound (IV-1) as a white solid. TLC (Hexanes:EtOAc 50:50): $R_f$=0.7; ¹H NMR (CDCl₃, 500 MHz) δ 10.01 (s, 1H), 7.93 (d, J=8.5 Hz, 1H), 7.87 (d, J=8.0 Hz, 1H), 7.63-7.59 (m, 2H), 7.56 (m, 1H), 7.19 (d, J=8.5 Hz, 1H), 6.47 (s, 2H), 4.29 (m, 1H), 3.84 (s, 3H), 3.79 (s, 6H), 3.49 (m, 2H); HRMS (ESI⁺): m/z calcd for C₂₂H₂₁NNaO₃S [M+Na], 402.114. found 402.115.

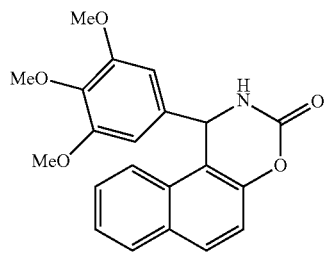

III-2

Chemical Formula: C₂₁H₁₉NO₅
Exact Mass: 365.13
Molecular Weight: 365.38

Purification by silica gel column chromatography (Hexanes:EtOAc 80:20 to 50:50) gave compound (III-2) as a white solid. TLC (Hexanes:EtOAc 50:50): $R_f$=0.7; ¹H NMR (CDCl₃, 500 MHz) δ 7.89-7.85 (m, 2H), 7.61-7.59 (m, 1H), 7.46-7.45 (m, 1H), 7.34 (d, J=9.0 Hz, 1H), 6.47 (s, 2H), 6.01 (m, 1H), 5.98 (m, 1H), 3.79 (s, 3H), 3.77 (s, 6H); HRMS (ESI⁺): m/z calcd for C₂₁H₁₉NNaO₅ [M+Na], 388.116. found 388.115.

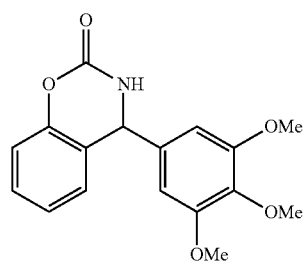

III-3

Chemical Formula: C₁₇H₁₇NO₅
Exact Mass: 315.11
Molecular Weight: 315.32

Purification by silica gel column chromatography (Hexanes:EtOAc 80:20 to 50:50) gave compound (III-3) as a white solid. TLC (Hexanes:EtOAc 50:50): $R_f$=0.7; ¹H NMR (CDCl₃, 500 MHz) δ 7.31-7.27 (m, 1H), 7.13-7.08 (m, 2H), 6.98-6.92 (m, 1H), 6.52 (s, 2H), 5.86 (s, 1H), 5.59 (s, 1H), 3.85 (s, 3H), 3.84 (s, 6H); HRMS (ESI⁺): m/z calcd for C₁₇H₁₇NNaO₅ [M+Na], 338.100. found 338.101.

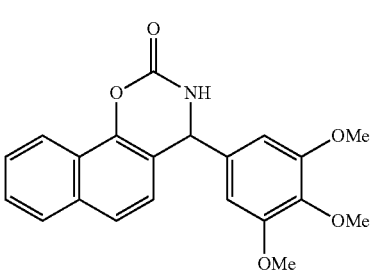

IV-5

Chemical Formula: C₂₁H₁₉NO₅
Exact Mass: 365.13
Molecular Weight: 365.38

Purification by silica gel column chromatography (Hexanes:EtOAc 80:20 to 50:50) gave compound (IV-5) as a white solid. TLC (Hexanes:EtOAc 50:50): $R_f$=0.7; $^1$H NMR (CDCl$_3$, 500 MHz) δ 8.38 (d, J=9.0 Hz, 1H), 7.81 (d, J=8.5 Hz, 1H), 7.62-7.54 (m, 3H), 6.95 (d, J=8.0 Hz, 1H), 6.56 (s, 2H), 5.74 (s, 1H), 5.55 (s, 1H), 3.86 (s, 3H), 3.84 (s, 6H); HRMS (ESI$^+$): m/z calcd for C$_{21}$H$_{19}$NNaO$_5$ [M+Na], 388.116. found 388.113.

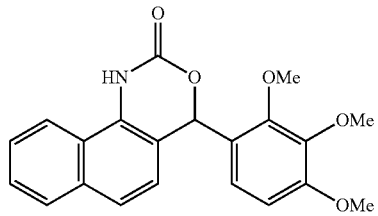

II-7

Chemical Formula: C$_{21}$H$_{19}$NO$_5$
Exact Mass: 365.13
Molecular Weight: 365.38

Purification by silica gel column chromatography (Hexanes:EtOAc 80:20 to 50:50) gave compound (II-7) as a white solid. TLC (Hexanes:EtOAc 50:50): $R_f$=0.7; $^1$H NMR (CDCl$_3$, 500 MHz) δ 8.19 (s, 1H), 7.89-7.86 (m, 2H), 7.62-7.60 (m, 1H), 7.58-7.51 (m, 2H), 6.98 (d, J=8.0 Hz, 1H), 6.88 (s, 1H), 6.78 (d, J=8.5 Hz, 1H), 6.59 (d, J=9.0 Hz, 1H), 3.95 (s, 3H), 3.91 (s, 3H), 3.85 (s, 3H); HRMS (ESI$^+$): m/z calcd for C$_{21}$H$_{19}$NNaO$_5$ [M+Na], 388.116. found 388.114.

1. Synthesis of Compound (II-4)

Naphthylisocyanate (5.9 mmol, 1.0 g) was added to a solution of t-butylisopropylamine (5.9 mmol, 0.9 mL) in diethyl ether (10 mL) under stirring at RT. The colorless solution was stirred for 3 hrs and subsequently cooled to 0° C. TMEDA (12.98 mmol, 2.0 mL) was added followed by n-butyllithium (11.8 mmol, 2.43M in hexanes, 3.0 mL). The clear yellow solution was stirred for 3 hrs during which time a white precipitate forms. The reaction mixture is cooled to −78° C., and the aldehyde (8.85 mmol, 1.7 g) in THF (5 mL) added drop-wise over four minutes. Following addition, ethanol (5 mL) was added rapidly and the mixture allowed to warm to RT and stirred for an hour. The reaction mixture is concentrated in vacuo, diluted with DCM and washed with saturated NH$_4$Cl). The organic layer will be evaporated onto silica and purified by column chromatography. Compound (II-4) was >96% pure by nuclear magnetic resonance spectroscopy.

2. Synthesis of Substituted 1,3-oxazin-2-ones (3) and 1,3-oxazin-2-thiones (4)

Figure 6:
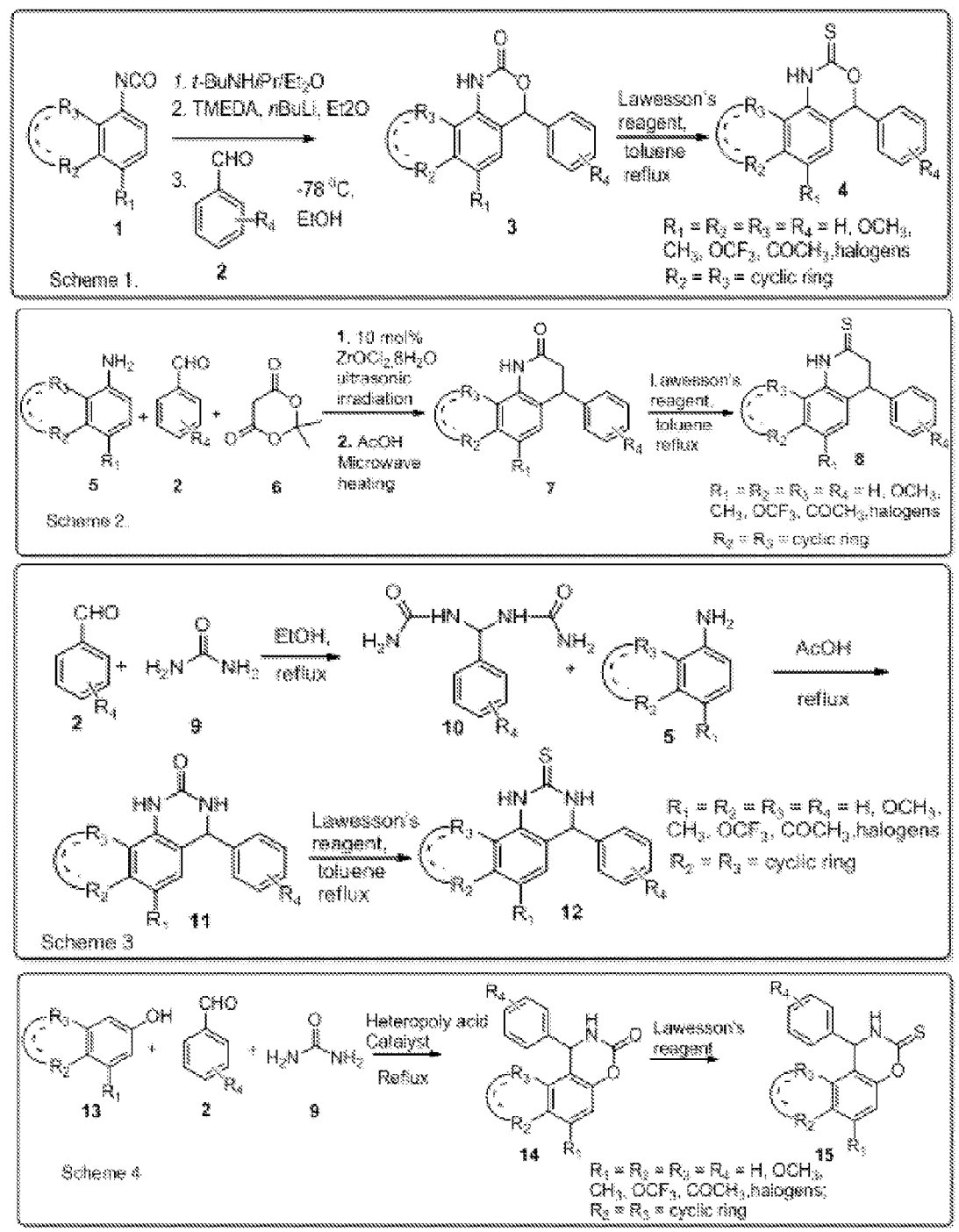
FIG. 6 shows synthetic schemes for preparation of paxillin inhibitors.

Referring to FIG. 6, analogs of substituted 1,3-oxazin-2-ones (3) and 1,3-oxazin-2-thiones (4) are synthesized by the established chemical method; various electron withdrawing groups (EWGs) and electron donating groups (EDGs) may be present on the aryl isocyantes as well as benzaldehydes. Commercially available substituted phenyl isocyanates (1) and substituted aryl aldehydes (2) are used to obtain the various substituted oxazin-2-ones (3). The chemical synthesis involves one pot, three steps, to obtain substituted oxazin-2-ones (3) in time efficient manner. Substituted phenyllisocyanates (1) are reacted with t-butylisopropylamine in diethyl ether. The formed urea intermediate is treated with TMEDA followed by n-butyllithium, then desired substituted arylaldehydes at −78° C., ethanol procure desired oxazin-2-ones (3). The oxazin-2-ones (3) are converted to the corresponding oxazin-2-thiones (4) by treating compounds 3 with Lawesson's reagent.

3. Synthesis of 3,4-dihydro-2(H)-quinolin-2-ones (8) and 3,4-dihydro-2(H)-quinolin-2-thiones (8)

Referring to FIG. 6, two methods are used: a) ultrasonic irradiation and b) microwave irradiation to prepare 3,4-dihydro-2(H)-quinolin-2-ones (7) and 3,4-dihydro-2(H)-quinolin-2-thiones (8). In the first method, a one pot method using ZrOCl$_2$.8H$_2$O catalyst under ultrasonic irradiation is used to obtain compounds (8) by reacting substituted anilines (5) with substituted benzaldehydes (2). The second method also utilizes microwave irradiation to prepare compounds (8). The 3,4-dihydro-2(H)-quinolin-2-ones are converted to corresponding quinolin-2-thiones (8) using the similar approach (Lawesson's reagent) used above.

4. Synthesis of 3,4-dihydroquinazolin-2(1H)-ones (11) and 3,4-dihydroquinazoline-2(1H)-thiones (12)

Referring to FIG. 6, nitrogen analogs (where X=NH) are prepared. The substituted benzaldehydes (2) are reacted with urea in ethanol under reflux conditions to obtain intermediate compounds (10). Compounds (10) are treated with substituted anilines (5) in acetic acid and refluxed to procure substitute 3,4-dihydroquinazolin-2(1H)-ones (11) which are converted to the corresponding thiones (12) using Lawesson's reagent. Alternatively the substituted 3,4-dihydro-2H-benzo[e][1,3]oxazin-2-one (14) and corresponding thiones (15) are prepared using a one pot method where substituted phenols (13), substituted aldehydes (2) and urea (9) are refluxed with a heteropoly acid catalyst. The final corresponding oxazinthiones (15) are synthesized using the approach described above.

5. Microsomal Stability

Microsomal stability of compound (II-4) (1 μM) was assessed in pooled liver microsomes (human, mouse, and rat) (FIG. 7). Briefly, compound (II-4) was incubated in duplicate with microsomes at 37° C. Reactions contained microsomal protein in 100 mM potassium phosphate, 2 mM NADPH, 3 mM MgCl2, pH 7.4. NADPH was omitted to detect NADPH-free degradation. At 60 minutes, the reaction was stopped by adding ice-cold methanol containing internal standard. Samples were centrifuged to remove precipitated protein, and the supernatants were analyzed by LC/MS/MS to quantitate the remaining parent.

6. P-450 Interaction Studies

CYP-450 interaction studies were conducted in pooled human liver microsomes (FIG. 8). CYP-450 inhibition (%) by compound (II-4) (1 μM) was compared to control inhibitors (1 μM) for the most common CYP-450 isoforms, CYP3A4, CYP2C9, CYP2D6, CYP2C19, and CYP1A2. There is a lack of significant inhibition of the most clinically relevant P-450 enzyme family members CYP3A4 and 2D6. Also, these data support the data in FIG. 7, which demonstrate that compound (II-4) is less susceptible to P-450 interaction in human microsomes compared to rodent.

7. Dermal Microemulsion

The microemulsion delivery system provides reliable non-invasive dose delivery when compared to standard IP injections. Moreover, dermal microemulsions provide sustained release providing more consistent drug levels with fewer doses, which will be valuable during multiple dose studies proposed herein. The dermal microemulsion comprises Capryol 90 (7.5% v/v), Triacetin (7.5% v/v), Cremophor EL (15% v/v), Transcutol P (15% v/v) generated via homogenization and water titration method. Physicochemical parameters include: viscosity of 29 mPa·s, average particle size of 97 nm, and pH of 6.5. Particle size remained relatively constant (100 nm) after 30 days at room temperature. Stability tests were performed on samples kept at RT, and additional stability tests were done on samples frozen at −20° C. and thawed to RT. The microemulsion formulation has acceptable viscosity, pH characteristics, particle size, and is stable at room temperature for at least 30 days.

8. Cell Lines and Growth Media

Cells:
Mel 270, primary-uveal melanoma (UM); OMM 2.5, metastatic-UM derived from same patient as Mel 270; OMM 1, metastatic-UM; 92.1 primary-UM tumor cell line. UM cell lines were kindly provided by Dr. Hans Grossniklaus, Emory Eye Center, Emory University, Atlanta, Ga. Primary human retinal microvascular endothelial cells (REC) were acquired from Cell System Corporation (Kirkland, Wash.).

Cell culture media requirements for Mel 270, OMM 2.5, and 92.1 UM cells: UM media contains RPMI-1640 (MediaTech, Herndon, Va.) supplemented with 10% Fetal Calf Serum (Hyclone, Logan, Utah), 1% L-Glutamine (200 mM) [Hyclone], 1% Sodium pyruvate (100 mM) [Lonza, Walkersville, Md.], 1% MEM Essential Vitamin Mix (100×) [Hyclone], 1% Non-Essential Amino Acids Mixture (100×) [Lonza, Walkersville, Md.], 1% 1M HEPES (Lonza), 1% of Penicilin G Sodium Salt/Streptomycin Sulfate/Amphotericin B Mix (100×) [Lonza] and 2-Mercapto Ethanol (lmL/L media v/v) [Gibco, Grand Island, N.Y.]. Media requirements for OMM 1 UM cells: DMEM (MediaTech) supplemented with 10% Fetal Calf Serum (Hyclone), 1% L-Glutamine (200 mM) [Hyclone], 1% Sodium pyruvate (100 mM) [Lonza], 1% MEM Essential Vitamin Mix (100×) [Hyclone], 1% Non-Essential Amino Acids Mixture (100×) [Lonza], 1% 1M HEPES [Lonza], 1% of Penicilin G Sodium Salt/Streptomycin Sulfate/Amphotericin B Mix (100×) [Lonza] and 2-Mercapto Ethanol (lmL/L media v/v) [Gibco].

Primary human retinal microvascular endothelial cells (REC, Lot 181) were acquired from Cell Systems Corporation (CSC, Kirkland, Wash.). Cells were grown on attachment factor (AF)-coated surfaces in M131 medium containing microvascular growth supplements (MVGS), gentamicin (10 mg/mL), and amphotericin B (0.25 mg/mL) (Invitrogen; Carlsbad, Calif.).

9. Apoptosis and Necrosis Analysis

Harvested cells were washed twice with cold PBS/2% FBS. Pelleted cells were resuspended in Annexin V Binding Buffer (BioLegend, San Diego, Calif.) at a concentration of $5.0 \times 10^6$ cells/mL following manufacturer's instructions. $5.0 \times 10^5$ cells (100 µL) were labeled with 5 µL of FITC Annexin V and 10 µL of Propidium Iodide (PI) solution. Cells were vortexed gently and incubated for 15 minutes at RT in dark. 300 µL of Annexin V Binding Buffer were added to each sample tube and analyzed in BD LSRII Flow Cytometry Analyzer (BD Biosciences, San Jose, Calif.). Apoptotic cells were defined as Annexin $V^+PI^{neg}$ while necrotic cells are defined as Annexin $V^+PI^+$. Experimental analysis was done using FlowJo xV10.0.6 software (Tree Star Inc., Ashland, Oreg.).

10. Flow Cytometry Analysis

Dead Cell Exclusion:
We used a 1:100 solution for up to $1.0 \times 10^6$ cells/100 µL of Zombie Aqua (BioLegend). Positivity indicates dye incorporation—cell death.

11. Adhesion Molecules Analysis

Harvested cells were washed and counted. $1.0 \times 10^6$ cells were labeled with the following cell surface antibodies: FITC anti-CD54 (ICAM-1, clone HA58, BioLegend), PE anti-CD102 (ICAM-2, clone CBR-IC2/2, BioLegend), PE-Cy7 anti-CD49d (VLA-4, clone 9F10, BioLegend), APC anti-CD106 (VCAM-1, clone STA, BioLegend), PerCP-Cy5.5 anti-CD166 (ALCAM, clone 3A6, BioLegend), Biotin anti-CD326 (EpCAM, clone 1B7, BD Biosciences) using manufacturer's conditions. Cells were incubated in antibody cocktail for 30 minutes on ice followed by two washes with PBS/2% FBS. Second-labeling step was performed using Brilliant Violet 421 Streptavidin (bv421-SA, BioLegend) for 30 minutes on ice followed by two washes as before. To control autofluorescence we used unlabeled cells. Isotype controls were used as negative controls and for antibody specificity. The following isotype controls were used: mouse IgG1 (clone MOPC-21, BioLegend) FITC, PE-Cy7, APC, by 421, APC; mouse IgG2a (clone MOPC-173, BioLegend) PE and rat IgG2b (clone RTK4530, BioLegend). Experimental analysis was done using FlowJo xV10.0.6 software (Tree Star Inc).

12. Phalloidin Analysis by Flow Cytometry

Retinal endothelial cells (REC) and UM-OMM 2.5 cells were harvested, washed and counted. $1.0 \times 10^6$ cells were fixed for 1 hr at 4° C. and permeabilized with the Intracellular Fixation and Permeabilization Buffer Kit (eBiosciences, San Diego, Calif.). Cells were washed followed by Alexa-Fluor 647 Phalloidin (MOLECULAR PROBES, Life Technologies, Carlsbad, Calif.) labeling using 1 U/µL. Cells were washed and analyzed using BD LSR II followed by analysis using FlowJo xV10.0.6 software.

13. Cellular Proliferation

Harvested cells were resuspended at a concentration of $1.0 \times 10^6$ cells/mL in warm PBS/1% FBS. Cells were labeled with 104 CFSE (Invitrogen) for 5 minutes at 37° C. then quenched on cold growth media (final volume 20 mL) for 10 minutes, twice. Cultured unlabeled cells were used as controls.

14. Gene Transcription Assays

RNA Isolation:
RNA from $1.0 \times 10^6$ UM cells was extracted using the QIAGEN miRNeasy Mini Kit (Qiagen, Valencia, Calif.). Briefly, cells were lysed and homogenized prior addition of chloroform. After centrifugation the upper colorless phase was transferred to clean tube followed by 100% ethanol precipitation. Extract was passed through a spin column followed by on-column DNase digestion. Column membrane was washed and RNase free water was used for RNA elution. RNA purity was assessed by analysis on nanodrop. RNA used met the following requirements: A260:A230 ratio greater than 1.7; A260:A280 ratio between 1.8 to 2.1 and concentration determined by A260>40 m/mL, as required by kit manufacturing company.

15. cDNA Synthesis

Genomic DNA elimination and cDNA synthesis was performed using QIAGEN $RT^2$ Easy First Strand kit. Briefly, 300 ng of RNA were mixed with Buffer GE2 (genomic DNA elimination buffer) and RNase free water to a final volume of 14.0 µL. RNA was incubated at 37° C. followed by quenching on ice. Material was incubated with Reverse Transcriptase Mix at 42° C. for 15 minutes followed by incubation at 95° C. for 5 minutes. Finished reaction was kept at −20° C. until ready to use.

16. PCR Analysis

A concise way to analyze for gene expression was chosen by selecting 84 genes highly associated with human Tumor Metastasis (PAHS-028ZF-2) and human Extracellular Matrix and Adhesion Molecules (PAHS-013ZF-2). The $RT^2$ Profiler PCR Array (QIAGEN) in a 96-well format to analyze for 84 different genes was used. cDNA synthesis reaction was mixed with a $2 \times RT^2$ SYBR Green Mastermix and RNase free water. A final volume of 25 µL was loaded onto each well. Plate was sealed and spun quickly to ensure no bubbles were present. The ROCHE LightCycler 480 was used to run the plate with the following cycling conditions: 1 cycle, 10 minutes, 95° C. for Hot Start followed by 45 cycles of 15 seconds at 95° C./1 minute at 60° C. to perform fluorescence data collection. Metastatic Uveal Melanoma (OMM 2.5) cells gene expression with a fold change greater than 2.0 compared to primary-UM (Mel 270) cells gene expression relative to GAPDH are emphasized. Data was analyzed using the SA Biosciences Web-based software.

17. Western Blot

REC, Mel 270, OMM 2.5 under Hepatocyte Growth Factor (HGF) or Vascular Endothelial Growth Factor (VEGF) stimulation conditions: Cell lysates were collected in RIPA lysis buffer (50 mM Tris-HCl, pH 7.4, 150 mM NaCl, 2 mM EDTA, 1% Nonidet P-40, 0.1% SDS) with protease 1× inhibitor cocktail (Roche; Indianapolis, Ind.). Lysates were kept on ice and centrifuged at 10,000×g×10 minutes and total protein was measured using the BCA assay (Pierce, Rockford, Ill.). Protein samples were mixed with 4×LDS loading buffer with 2.5% 2-mercaptoethanol (Sigma-Aldrich), heated to 70° C. for 10 minutes, and loaded on NuPAGE 4-12% Bis-Tris gel (Invitrogen, Carlsbad, Calif.). Immunoblotting was performed with nitrocellulose membranes (Bio-Rad, Hercules, Calif.) at 170-mA start and 110-mA end at 25 V for two hours in NuPAGE transfer buffer (Invitrogen) containing 20% methanol. Membranes were blocked using Odyssey blocking buffer (LI-COR; Lincoln, Nebr.) for one hour at room temperature with gentle shaking Membranes were then incubated at 4° C. with specific primary antibodies (1:1000) overnight. Cellular protein was normalized using rabbit-GAPDH or mouse-α-Tubulin [1:20,000] (Cell Signaling, Danvers, Mass.; LI-COR, respectively). Secondary antibodies (IRDye 800CW goat anti-rabbit and IRDye 680LT goat anti-mouse) [1:10,000] were incubated in the dark at room temperature for 45 minutes. Dual-channel infrared scan and quantitation of immunoblots were conducted using the ODYSSEY Sa infrared imaging system with Image Studio (Ver. 3.1.4) (LI-COR).

18. Scratch Wound

The effect of compound (II-4) on HGF-induced migration of UM cells was evaluated by scratch wound assay. In brief, confluent UM cell monolayers were wounded using a 100 µL yellow micropipette tip after cells were cultured in appropriate media for 24 hrs. Cells were rinsed with PBS to remove detached cells and incubated with serum-free medium containing appropriate concentration of HGF with or without compound (II-4) (104). Wound closure was monitored under an inverted phase contrast microscope, and then photographed in digital format (×50) after incubation for 24 hrs. For quantitative assessment, the wound area was determined by software 5.1 Image-Pro Plus (Media Cybernetics, Inc., Silver Spring, Md.).

Figure 2:
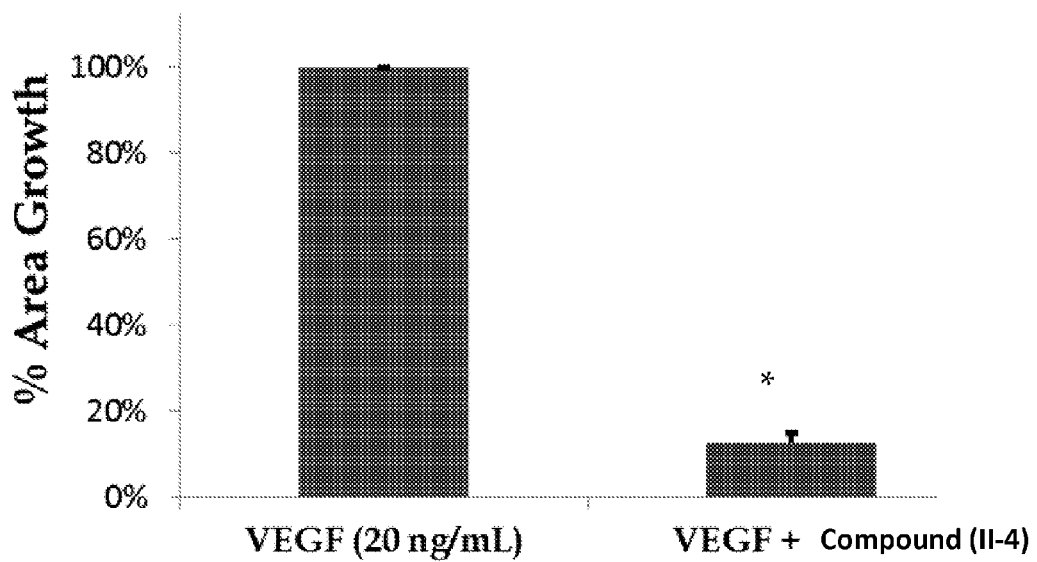
FIG. 2 shows results of a retinal endothelial cell (REC) scratch-wound assay.

FIG. 2 shows results of an REC scratch-wound assay. RECs were wounded and treated with VEGF (20 ng/mL) and either compound (II-4) (1 µM) or vehicle. Compound (II-4) reduced migration by ~10-fold when measured 24 hrs post-scratch. (*P<0.001; n=6).

19. Statistical Analysis

All data in the different experimental groups are expressed as mean+/−SD and obtained from at least three independent experiments. Analysis of variance (ANOVA) was used to assess the statistical significance of the differences between groups, followed by Duncan's multiple-range test or Student's t-test, where appropriate. P value of <0.05 was considered significant.

20. Primary-UM Tumor Cells in Culture Show Higher Levels of Spontaneous Apoptosis than Metastatic-UM Tumor Cells Apoptosis is speculated to contribute to different aspects of neoplastic disease including, but not limited to tumor progression and anti-cancer therapy. More apoptotic cells may be present in primary-UM than metastatic-UM as these cells respond to radiation-induced cell death. The ability of primary- and metastatic-UM (Mel 270 and OMM 2.5, respectively) cell lines to spontaneously apoptose was measured—the insult being the harvesting process, by measuring Propidium Iodide (PI) versus Annexin V labeling followed by flow cytometry analysis. Results in FIG. 9 show increased susceptibility of primary-UM cell lines to apoptosis (Apoptosis phenotype is defined as $PI^{neg}$ Annexin $V^+$) showing 18% fold difference (14.1%±1.36% of Mel 270 cells and 0.8%±0.15% OMM 2.5). Cell injury can induce necrosis, recently considered a block for in vivo anti-tumor $CD8^+$ T cell dependent immune responses. The levels of necrosis were measured as defined by $PI^+$ Annexin $V^+$. Mel 270 showed a significant increase in the average percentage necrotic cells over OMM 2.5 (21.9%±2.0% versus 6.5%±2.2%, respectively; p=0.002, n=4). In keeping with prior studies, this suggests Mel 270, a primary tumor UM cell line, is more susceptible to spontaneous apoptosis in comparison to OMM 2.5, its metastatic counterpart.

FIG. 9 shows that the primary UM cell line Mel 270 shows high percentage of spontaneous apoptosis compared to metastatic OMM 2.5 cells (upper, representative of n=4; lower, quantitation with SD). Cultured cells were labeled with 54 Annexin V-FITC and 104 PI in BioLegend Binding Buffer for 15 minutes prior flow cytometry analysis. Apoptosis defined as PI$^{neg}$ Annexin V$^+$. Necrosis defined as PI$^+$ Annexin V$^+$. Data acquisition was done in BD LSRII Flow Cytometer.

21. Differential Expression of Genes Associated with Adhesion, Tumor Invasion and Immunosuppression in Primary-Versus Metastatic-UM Tumor Cells In search for designing a potential adjuvant therapy for UM patients gene expression was analyzed in primary-versus metastatic-UM cell lines using a specific cohort of genes associated with adhesion, invasion and metastasis. Rather than transcript quantitation, results were expressed as the ratio of metastatic UM relative to primary UM, normalized to GAPDH. The lists of genes analyzed include inflammation-, adhesion- and metastatic pathways (FIG. 10 and FIG. 11). Notably, differential expression of integrins and their receptors between primary- and metastatic-UM was found. The transcriptional assay identified the alpha-4 (α4) integrin (ITGA4) as differentially regulated in primary- and metastatic-UM. Engagement of α4 induces actin cytoskeletal-rearrangement. Expression of the α4 was specific, as other members of the Alpha-integrin (ITGA) family, such as ITGA3, ITGA6, ITGA7, were not highly expressed in primary-versus metastatic-UM. Transcriptional analysis revealed TGFB1 and VEGFA genes, to show a higher ratio of metastatic-UM relative to primary-UM. These genes are associated with immunosuppression and angiogenesis, respectively. Collectively, we found inflammation-, adhesion- and invasion-associated genes to exhibit a higher primary-versus metastatic-UM ratio, whereas genes associated with dampening of immune responses showed a higher ratio in metastatic-relative to primary-UM analysis.

22. High α4 Integrin Protein Levels in Primary-UM Tumor Cells that Become Metastatic Uncoupling of transcription and protein levels were previously identified after modulation of the actin cytoskeleton. Next, the protein levels of α4 and other integrin subunits and cytoskeletal remodeling in UM cell lines were examined. The protein levels of a cohort of integrins associated with intracellular signaling cascades in cancer, the cytoskeleton and targets of immunotherapy were analyzed. The protein expression of surface bound Intercellular Adhesion Molecule-1 and -2 (ICAM-1, ICAM-2—aka CD54 and CD102, respectively), Vascular Cell Adhesion Protein-1 (VCAM-1—aka CD106), Epithelial Cell Adhesion Molecule (Ep-CAM—aka CD326), Activated Leukocyte Cell Adhesion (ALCAM—aka CD166) and Very Late Antigen-4 (VLA-4—aka CD49d) was assessed in primary- and metastatic-UM tumor cell lines by flow cytometry (FIG. 12). To increase accuracy in the analysis dead cells were excluded by using an amine reactive fluorescent dye non-permeant to live cells (ZOMBIE AQUA—BioLegend). Dead cells tend to bind non-specifically to many antibodies, giving rise to false positive results. Then, the expression of the aforementioned proteins was analyzed. From the examined cohort, a significant difference was observed in protein levels of CD49d (FIG. 12B) between primary and metastatic UM. Anti-CD49d is commonly used for VLA-4 detection, an integrin composed of the α4 and α1 subunits. Specifically, anti-CD49d recognizes the α4 subunit. Thus, the protein expression analysis correlates with the transcriptional studies, as higher levels of ITGA4 (α4) transcripts and CD49d (α4) protein levels were observed in primary-UM relative to metastatic-UM.

About 50% of UM primary tumors metastasize. The mechanisms driving metastases in the primary tumors are not well understood. To investigate if the α4 subunit of VLA-4 could potentially be a target in the mechanisms driving metastases VLA-4 protein levels were tested in a primary-UM cell line that never metastasized, 92.1. The 92.1 cell line was cultured and examined by flow cytometry analysis parallel to the primary- and metastatic-UM cell lines Mel 270 and OMM 2.5, respectively, as shown in FIGS. 12C-D, and data not shown. Interestingly, levels of VLA-4 in 92.1 and OMM 2.5 were similar. In contrast, the percentage of VLA-4$^+$ cells in Mel 270 were much higher. This suggests VLA-4 regulation may be critical for the transition of melanocyte transformation and further migration. Next, a second metastatic-UM cell line, OMM 2.1, was analyzed for VLA-4 levels (FIGS. 12C and 12D). Similar to our previous results, there are a lower percentage of cells with VLA-4 positivity. Collectively, we identified the α4 integrin subunit as a unique molecule, previously unpublished, regulated differently in primary cells that metastasize versus those without detectable metastasis and metastatic UM.

23. Targeting α4 Integrin-Downstream Signaling Through Paxillin Inhibition

Figure 13:
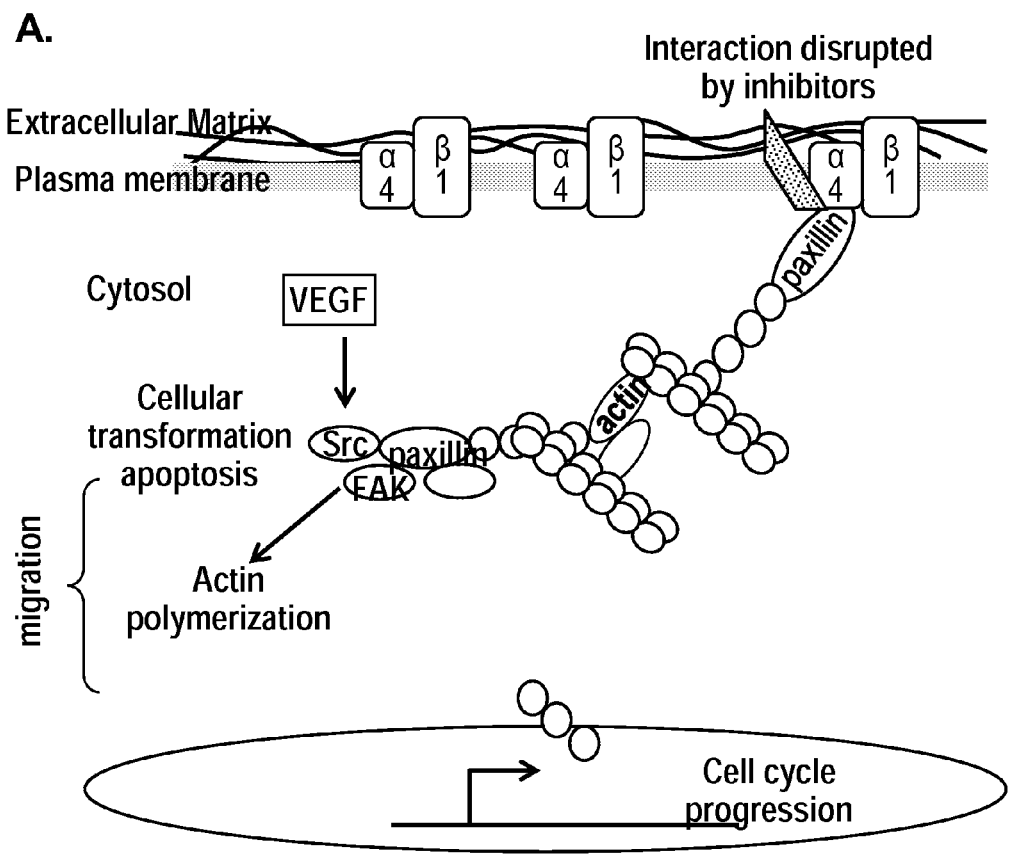
FIG. 13 shows that compound (II-4) inhibits pY118 without increasing apoptosis in REC: panel A is a diagram showing a concise version of paxillin-downstream signaling and compound (II-4) intervention within pathway; panel B shows that VEGF-induced paxillin phosphorylation (pY118) is reduced by paxillin inhibitor treatment (compound (II-4)); panel C shows quantitation of the VEGF-induced paxillin phosphorylation (pY118) of FIG. 13, panel B; and panel D shows flow cytometric analysis of treated and untreated REC labeled with Annexin V and PI.

The α4 subunit of the cytoplasmic tail of VLA-4 interacts with the cytoskeletal adaptor paxillin, merging intracellular signaling events that drive cellular proliferation and migration (FIG. 13). Compound (II-4) inhibits phosphorylation of paxillin at Y118 (pY118) in the LD-region that interacts with the α4 subunit of VLA-4. To confirm the inhibition of pY118 of paxillin after use of compound (II-4) retinal endothelial cells (REC) were activated with Vascular Endothelial Growth Factor (VEGF) at 50 ng/mL in the presence or absence (vehicle) of compound (II-4) at a concentration of 104 for 4-hrs. Lysates were collected, and, as seen in FIG. 13B, phosphorylation levels were measured by Western Blot. VEGF-induced pY118 was prevented by treatment with compound (II-4) [VEGF-REC treatment versus untreated, *p<0.005; VEGF-induced versus compound (II-4) treatment, **p<0.05—FIG. 13C].

Next, the use of the compound (II-4) to increase apoptosis in normal REC was tested. Cultured cells received compound (II-4) or vehicle at a concentration of 1 µM for 4-hrs followed by PI and Annexin V labeling and flow cytometry analysis. Treatment with compound (II-4) did not cause an increase in spontaneous apoptosis in REC as shown in FIG. 13D.

24. Increased Expression of Total Paxillin and Significant Reduction of pY118 Paxillin in Metastatic-UM Cells Treated with Compound (II-4)

In FIG. 13 it was demonstrated that compound (II-4) inhibits pY118 without increasing apoptosis in REC. Immune studies of the α4β1 integrins (VCAM-1 and VLA-4) show high affinity α4 integrins may initiate signaling cascades through paxillin that regulate leukocytes migration to inflammation sites. Metastatic UM show reduced levels of α4 integrin (FIGS. 14A-B). Blocking phosphorylation of paxillin in a cell with lower protein abundance may block downstream signaling in both primary and metastatic UM. The levels of total paxillin and pY118 were measured after activation of metastatic-UM (OMM 2.5) cells with Hepatocyte Growth Factor (HGF) to address in vitro if disruption of α4-downstream signaling through paxillin can affect α4-downstream signaling. It is known HGF enhances PI3K-dependent migration of UM cells. FIGS. 14A-B shows compound (II-4) dramatically decreased the ratio of pY118 paxillin to total paxillin (pPax:Pax) in HGF-treated metastatic-UM cells, blocking the α4-paxillin downstream signaling.

25. Reduction in Proliferation in UM Tumor Cell Lines after Treatment with a Paxillin Inhibitor Treatment with compound (II-4) showed a reduction in total cell numbers compared to untreated cultures. Next, it was investigated if reduced numbers were a consequence of a reduction in UM cells proliferation. Cell cultures in the presence or absence of compound (II-4) were analyzed by follow cytometry for cytoskeletal fragmentation and proliferation. Uncontrolled cytoskeletal remodeling and cell proliferation are considered hallmarks of tumor growth and metastasis. To test if inhibition of paxillin affects cytoskeletal remodeling and cell proliferation, UM cell lines were labeled with phalloidin, a toxin that binds filamentous actin (F-actin), indicative of actin remodeling. Cultured cells were fixed and permeabilized followed by intracellular labeling. The amount of intracellular phalloidin reflected the amount of cellular F-actin. The results showed no difference in actin remodeling in the examined UM tumor cells after treatment (FIG. 15A). A difference in actin remodeling was not expected as it is known that there are multiple mechanisms merging into actin polymerization. Although blockade of α4-paxillin show no difference compared to untreated cells we observed a difference between primary- and metastatic-UM cell lines in the abundance of F-actin. To address if differences are only reflective of primary versus secondary tumor cell lines, 92.1 primary-UM cells that do not metastasize with pahalloidin were labeled. Results in FIG. 15B show a similar trend between secondary (metastatic UM) and primary tumor that does not metastasize. Actin remodeling was inversely proportional to α4 protein expression. Modulation of paxillin does not affect VLA-4 protein, shown in FIG. 15C.

To test the hypothesis that inhibition of paxillin will reduce cellular proliferation UM cell lines were labeled with carboxyfluorescein succinimidyl ester (CFSE), a cell tracking dye, and cultured for 96 hrs. A group of cells received treatment with compound (II-4) for the last 24 hours. Maximum CFSE fluorescence was controlled using labeled cells prior culture –0 hr. Negative control was established using unlabeled cells cultured in parallel. Histograms in FIG. 15D show 96 hrs cultured cells divided with a 1-log shift or reduction in CFSE intensity. Both primary- and metastatic-UM cell lines showed this shift suggesting all cells divided, depicted in dotted line. Treatment with compound (II-4) caused a reduction in cell proliferation in Mel 270 primary-UM cells. This reduction was not observed in metastatic-UM cell, suggesting a specific effect in cell proliferation by the inhibitor. Cell proliferation was not affected in the 92.1 cell line. These results suggest cytoskeletal fragmentation is not affected by treatment with compound (II-4), but cellular proliferation does. The effects are selective, as the primary cell line that metastasize (Mel 270) show reduction in proliferation and not the non-metastatic one (92.1).

26. Compound (II-4) Inhibits VEGF-Induced Migration and Proliferation of Endothelial Cells Two methods of evaluating VEGF-induced REC migration were used to assess the impact of compound (II-4) on paxillin-mediated migration: the scratch assay and the transwell (Boyden chamber) cell migration assay. To test if paxillin inhibition would reduce VEGF-induced REC migration, RECs were wounded and treated with VEGF (100 μg/mL) +/− compound (II-4) (100 μM to 10 μM). Wound closure was monitored by phase microscopy over 24 hours and area of wound closure was calculated using the sophisticated image analysis tools in Adobe Photoshop. Cells were then fixed and nuclei were stained using DAPI to show extent of cell migration. Measurements of wound closure at 24 hours reveal a concentration-dependent inhibition of migration with compound (II-4) (IC50=181 nM) (FIG. 17A).

Compound (II-4) was further investigated around these concentrations using the transwell migration assay (FIG. 17B). After 24 hours of VEGF (100 μg/mL) stimulation, a significant decrease is observed in migration RECs (P<0.001).

To investigate the potential of compound (II-4) affecting the proliferative capacity of RECs treated with VEGF, proliferation was measured using the metabolic assay based on the tetrazolium salt, WST-1. A significant decrease was observed in VEGF-induced cellular proliferation with increasing concentrations of compound (II-4) (FIG. 18A; P<0.0001). To rule out the possibility that this observation was related to cytotoxicity, RECs were incubated with a high concentration of compound (II-4) (1 μM) for 24 hours. Cells were harvested and apoptosis measured with Annexin-V/Propidium Iodide (PI) staining and analyzed using flow cytometry. No evidence of apoptosis was detected (FIG. 18B).

27. Compound (II-4) does not Inhibit Integrin-Dependent Cell Attachment

Figure 19:
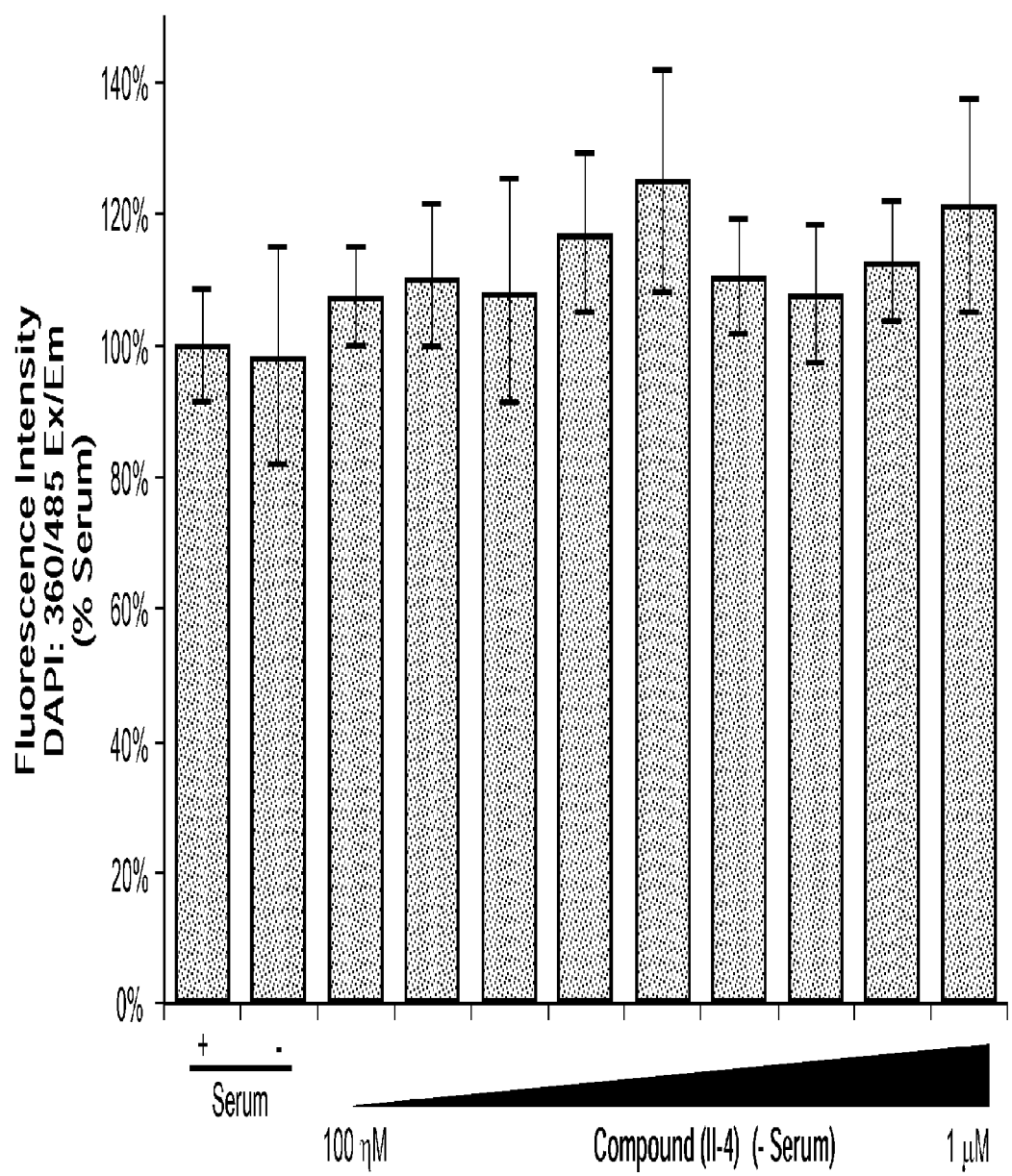
FIG. 19, shows that compound (II-4) at concentrations ranging from 100 nM to 1 µM did not impede the attachment of RECs.

Adhesive interactions with extracellular matrix proteins rely on focal adhesion proteins engaging with integrins to strengthen and maintain cell contacts. In the transwell migration assay system, initial cell-attachment to the porous membrane was relied upon in order to obtain a measure of cells that have migrated through to the underside of the well. Since compound (II-4) was in direct contact with cells prior to being seeded onto the transwell membranes, the potential of compound (II-4) to impede the attachment of RECs to the membranes was investigated. After six hours, the ability of RECs to seed to the attachment-factor coated wells was not impeded with increasing concentration of compound (II-4) (FIG. 19). These results indicated that inhibition of VEGF-mediated cell migration with compound (II-4) is not due to preventing initial cell-attachment to basement membranes, but through disruptions in VEGF migratory signaling mechanisms. However, investigation of integrin-mediated signaling may be of interest to further evaluate and characterize compound (II-4)'s potential role in disrupting cross-talk between growth-factor and integrin-mediated signaling during pathological retinal angiogenesis.

28. VEGF Activates the Src/FAK/Paxillin/ERK Signalsome in RECs

Figure 20:
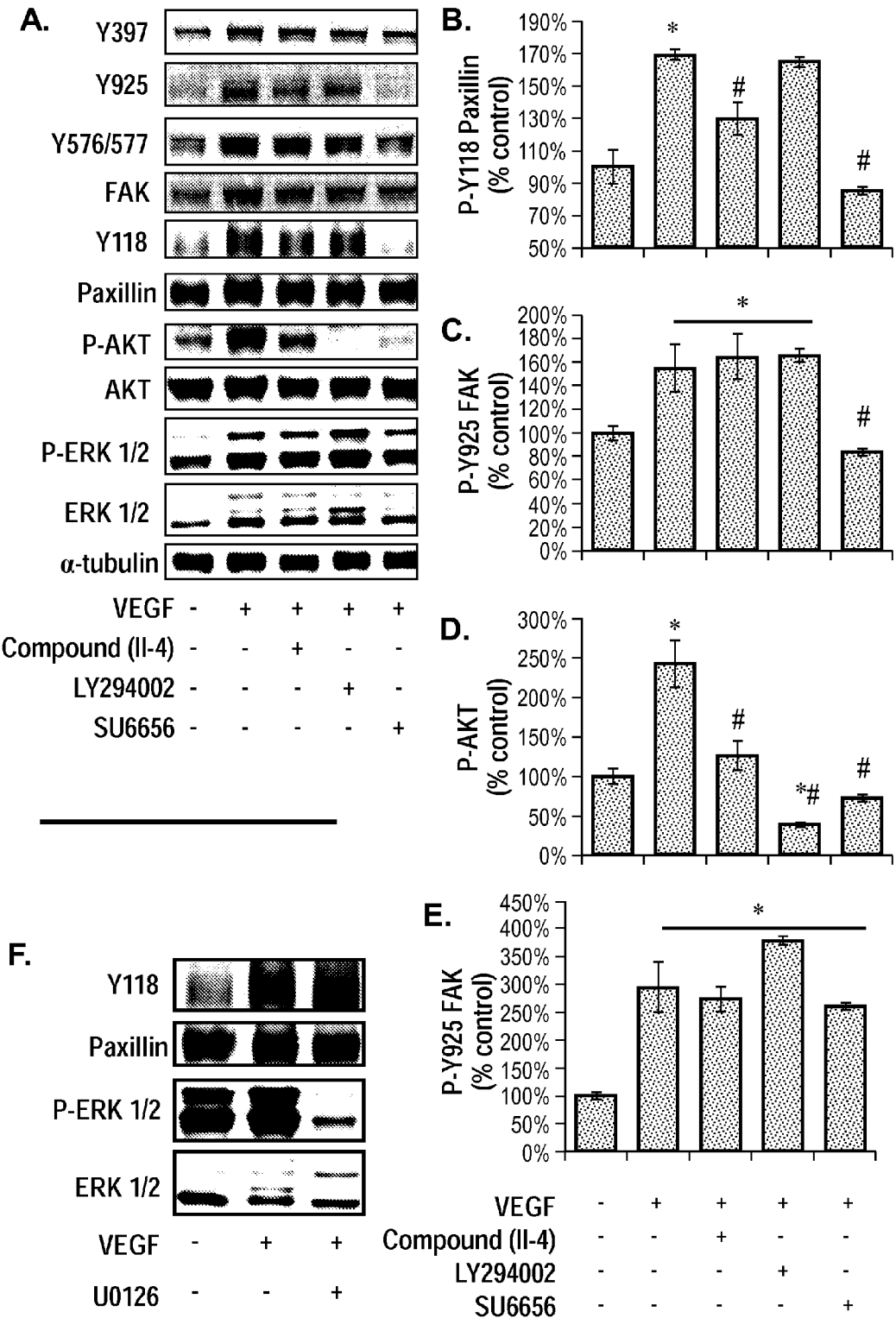
FIG. 20, panel A, shows VEGF-induced activation of Src/FAK/Paxillin signalsome in the presence of compound (II-4), LY294002, or SU6656; panel B quantifies the phosphorylation of paxillin observed in panel A; panel C quantifies the phosphorylation of FAK observed in panel A; panel D quantifies the phosphorylation of AKT observed in panel A; panel E quantifies the phosphorylation of ERK1/2 observed in panel A; and panel F shows that ERK's involvement in VEGF-induced REC proliferation was independent of paxillin Y118 activation.
Figure 21:
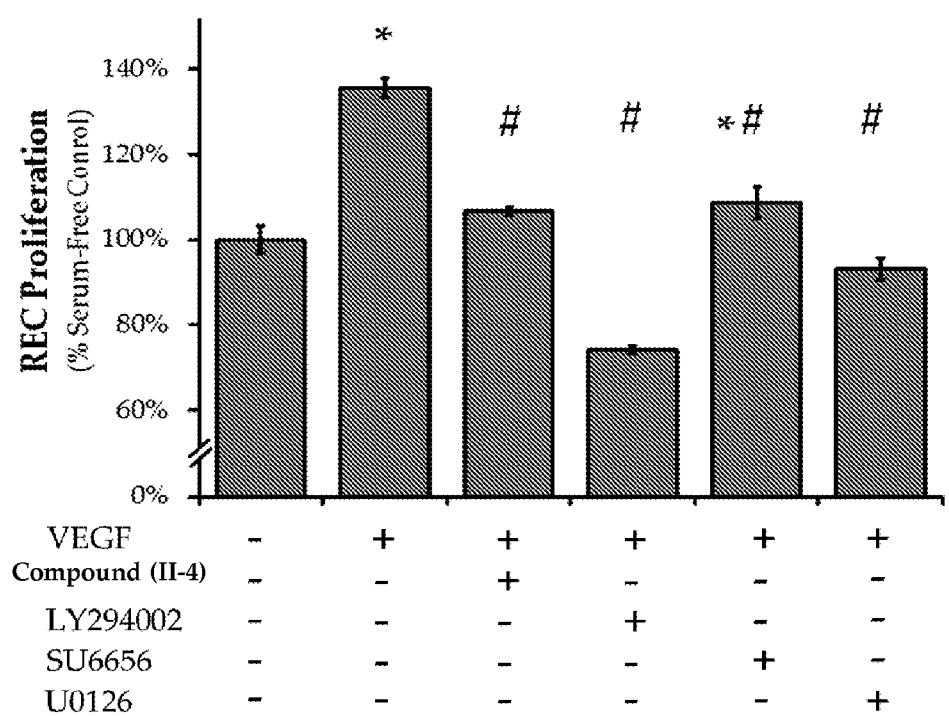
FIG. 21 shows that compound (II-4) inhibits VEGF-induced REC proliferation.

In RECs, it was shown that VEGF-induced autophosphorylation of FAK Y397 led to further activation of Src-dependent FAK tyrosine residues 576/577 and 925. The Src/FAK complex in turn drove phosphorylation of binding partner paxillin at Y118 and downstream proliferation marker, P-AKT (FIG. 20A-D). AKT was validated as a downstream readout of the signalsome's activity in RECs using LY294002, an inhibitor of PI3K, which did not affect Src-activation of either FAK or paxillin (FIG. 20B,C). Using the Src inhibitor SU6656 (1 µM), it was confirmed that autophosphorylation of FAK Y397 was independent of Src and that FAK (Y576/577 and 925), paxillin (Y118), and downstream AKT (Ser473) phosphorylation was dependent on Src activity (FIG. 20). According to this mechanism, these data have demonstrated that VEGF-induced proliferation requires Src-dependent activation of FAK and paxillin, driving proliferation through AKT (FIG. 21).

ERK-dependent proliferation has been confirmed in multiple cell types, including endothelial cells. One such mechanism involves ERK-mediated serine-83 phosphorylation of paxillin to promote disassembly of FAK and paxillin in FAs. ERK's involvement was validated in VEGF-induced REC proliferation was independent of paxillin Y118 activation using the inhibitor U0126 (FIG. 20F). There was no change in activation of Y118 with U0126 but VEGF-induced REC proliferation was inhibited (FIG. 21). Moreover, SU6656 was used to demonstrate that Src-dependent REC proliferation was independent of ERK1/2 activation (FIG. 20E). These data indicate that Src and ERK act independently on paxillin to coordinate FA turnover that drives VEGF-induced REC proliferation, as shown in model FIG. 1A.

VEGF-induces RNV. VEGF-activation of its receptor, VEGF-R2 (KDR/FLK1) promotes FA assembly through Src/FAK mediated phosphorylation of paxillin at Y118. Parallel activation of ERK drives disassembly through S83 phosphorylation causing the complex to dissociate. Together, these signaling events drive FA turnover and thus, angiogenesis.

29. Compound (II-4) Inhibits Y118 without Altering Src/FAK Complex Activation or ERK Activation Compound (II-4) potently inhibits VEGF-induced migration and proliferation of RECs (FIGS. 17 and 18). To gain insight into the mechanistic basis for this phenotype, the effect of compound (II-4) on the Src/FAK/paxillin/ERK signalsome in RECs under VEGF was examined. First, it was determined that compound (II-4) was able to inhibit VEGF-induced PaxY118 phosphorylation (FIG. 20B). Then, it was further shown that compound (II-4)'s activity was independent of both FAK Y397 autophosphorylation and Src-driven FAK Y925 (FIG. 20C). However, compound (II-4) was able to prevent Src/FAK/paxillin complex-dependent activation of AKT, similar to Src inhibition (FIG. 20D). Together, compound (II-4)'s effect on Y118 and downstream P-AKT strongly suggest the inhibition of Src/FAK/paxillin FA assembly. Next, characterization of the potential of compound (II-4) to affect FA disassembly through inactivation of ERK was explored. No significant change was revealed in ERK1/2 phosphorylation levels in RECs (FIG. 20E). One possible explanation for these data is that compound (II-4) disrupts FAK binding to the LD2/4 domains of paxillin, thus preventing Src access to paxillin Y118 while allowing uninterrupted activity of ERK on serine 83 of paxillin. These two signaling mechanisms turn off assembly and turn on disassembly of FAs during VEGF-induced REC proliferation (FIG. 21). Altogether, these data raise the possibility that compound (II-4) induces allosteric changes in paxillin effectively disrupting the interactions within the Src/FAK/paxillin/ERK signalsome halting FA turnover and VEGF-mediated angiogenesis.

30. Efficacy in Murine OIR Model

Topical delivery of compound (II-4) using an ocular ME was chosen for several reasons. First, intravitreal injection is technically challenging and, unlike intraocular delivery of proteins, is unnecessary for delivery of small molecules. Second, safe and effective ocular delivery of drugs to humans using ME technology has been demonstrated, e.g., Restasis (cyclosporine), and there are 55 human clinical trials that have/are utilized this technology for topical or systemic drug administration (source: clinicaltrial.gov). The murine OIR model was used to examine the effect of compound (II-4) on the natural history of VEGF-induced proliferative retinopathy. Briefly, pups were exposed to 75% oxygen at post-natal day 7 (P7) for 5 days and then returned to normal oxygen at P12. Mice received daily ocular administration of either compound (II-4) (0.5 mg/kg or 5 mg/kg) or vehicle (ME) from P12 to P17. Eyes were enucleated at P17 and retinal whole-mounts stained for endothelial cells followed by quantification of avascular area and vascular tuft formation. There was a striking inhibition of hypoxia-induced neovascularization coupled with a modest increase in retinal avascular area in both compound (II-4)-treated groups when compared to vehicle-controls (FIG. 22A). Western blot examination of retinal homogenates revealed a dose-dependent reduction in total paxillin (FIG. 22B).

31. Microsomal Stability

Microsomal stability of compound (II-4) (1 µM) was assessed in pooled liver microsomes (human, mouse, and rat) (FIG. 23). Briefly, compound (II-4) was incubated in duplicate with microsomes at 37° C. Reactions contained microsomal protein in 100 mM potassium phosphate, 2 mM NADPH, 3 mM MgCl2, pH 7.4. NADPH was omitted to detect NADPH-free degradation. At 60 min, the reaction was stopped by adding ice-cold methanol (+ internal standard). Samples were centrifuged to remove precipitated protein, and the supernatants were analyzed by LC/MS/MS to quantitate the remaining parent. Compound (II-4) was rapidly metabolized by mouse, rat, and human cytochrome P-450 enzymes.

32. P-450 Interaction Studies

CYP-450 interaction studies were conducted in pooled human liver microsomes (FIG. 24). CYP-450 inhibition (%) by compound (II-4) (1 µM) was compared to control inhibitors (1 µM) for the most common CYP-450 isoforms, 3A4, 2C9, 2D6, 2C19, and 1A2. Compound (II-4) lacks significant inhibition of the most clinically relevant P-450 enzyme family members 3A4 and 2D6.

33. Off-Target Screening

Counter-screen assays to determine "off-target" effects are conducted at an early stage to mitigate toxicological risk of new chemical entities. Compound (II-4) (10 µM) counter screening was conducted against a wide variety of target receptors, enzymes, and ion channels using a serum-free cell-based assay, ExpresS Profile (Eurofins, Cerep Panlabs). Inhibition >50% is considered a "positive" interaction. The serotonin receptor 5-HT2B and the melatonin-1 receptor (MT-1) were identified as possible binding targets for compound (II-4) (FIG. 25).

Compound (II-4) inhibits VEGF-induced migration and proliferation of retinal endothelial cells. Compound (II-4) inhibits VEGF-induced paxillin phosphorylation (Y118) leading to disruption of the Src/FAK/paxillin signalsome; a critical signaling hub for migration and proliferation in hyperproliferative disorders. Compound (II-4) mitigates retinal neovascularization following ocular administration in the murine OIR model. Compound (II-4) dose-dependently decreases paxillin expression in retinal homogenates in the murine OIR model. Compound (II-4) undergoes significant in vitro metabolism by cytochrome P-450s, which is ideal for ocular delivery.

FIGURE LEGENDS

Figure 1B:
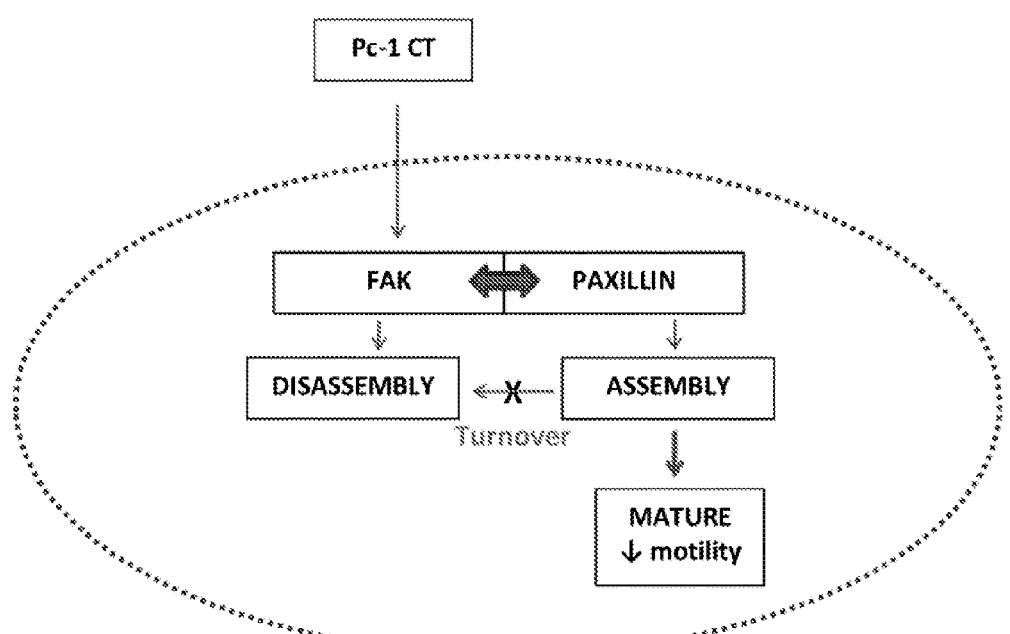
FIG. 1B is a schematic showing that focal adhesion (FA) turnover is impaired in polycystic kidney disease (PKD).

FIG. 1A: VEGF-induced RNV. VEGF-activation of its receptor, VEGF-R2 (KDR/FLK1) promotes FA assembly through Src/FAK mediated phosphorylation of paxillin at Y1 18. Parallel activation of ERK drives disassembly through S83 phosphorylation causing the complex to dissociate. Together, these signaling events drive FA turnover and thus, angiogenesis.

FIG. 1B: FA turnover is impaired in PKD. In the absence of the cytoplasmic tail (CT) of PC-1, FAs are formed without FAK which leads to reduced FA disassembly and motility.

FIG. 2: REC scratch-wound assay. RECs were wounded and treated with VEGF (20 ng/mL) and either compound (II-4) (1 µM) or vehicle. Compound (II-4) reduced migration by ~10-fold when measured 24 hrs post-scratch. (*P<0.001; n=6)

FIG. 3: Immunohistochemical analysis of paxillin in ADPKD mouse kidneys. Darker labeling indicated localization in the cystic epithelial cells as determined by DAB staining (B). No staining was observed in the negative control section (A). Magnification 40×.

FIG. 4: Paxillin in ADPKD kidneys. (A) Immunoblot of total paxillin in protein lysates from non-cystic Pkd1$^{+/+}$ (n=5) and cystic Pkd1$^{V/V}$ (n=3) mouse kidneys at post-natal day 11 after 8 days of dermal application of compound (II-4) microemulsion solution. GAPDH was used as a loading control. Densitometry of the bands normalized to GAPDH is shown for (B) paxillin and (C) phospho-paxillin (C). * P<0.005 difference between groups.

FIG. 5: Reduction in cyst progression after treatment with paxillin inhibitor compound (II-4).

FIG. 7: Compound (II-4) microsomal stability.

FIG. 8: Cytochrome P-450 interaction studies using human microsomes.

FIG. 9: The primary UM cell line Mel 270 shows high percentage of spontaneous apoptosis compared to metastatic OMM 2.5 cells. Cultured cells were labeled with 5 µL Annexin V-FITC and 10 µL PI in BioLegend Binding Buffer for 15 minutes prior flow cytometry analysis. Apoptosis defined as PI$^{neg}$ Annexin V$^+$. Necrosis defined as PI$^+$ Annexin V$^+$. Data acquisition done in BD LSRII Flow Cytometer. Upper, representative of n=4. Lower, Quantitation with SD.

FIG. 10: Fold expression of gene transcripts metastatic UM (OMM 2.5) relative to primary UM (Mel 270) cell line. Analysis performed using RT$^2$ Profiler Array, normalized to GAPDH. Results representative of n=3.

FIG. 11: Fold expression of gene transcripts primary UM (Mel 270) relative to metastatic UM (OMM 2.5) cell line. Analysis performed using RT$^2$ Profiler Array, normalized to GAPDH. Results representative of n=3.

FIG. 12: Protein levels of a cohort of integrins associated with adhesion and signaling. UM cell lines were cultured, harvested and labeled with a cohort of fluorescently-tagged antibodies against adhesion molecules for flow cytometric analysis. A, Increased VLA-4 protein levels by primary UM (Mel 270) cell line compared to its metastatic counterpart (OMM 2.5). Representative histogram of n=4. B, Quantitation of all experiments +/−SD. C, VLA-4 protein levels are similar in metastatic UM (OMM 2.1) and primary UM (92.1) that does not metastasize. Representative histogram of n=3. D, Quantitation of all experiments +/−SD. Cell surface expression was examined by flow cytometry.

FIG. 13: Targeting the alpha-4 subunit of VLA-4 signaling through inhibition of paxillin. A, Adapted diagram from Salgia showing a concise version of paxillin-downstream signaling and compound (II-4) intervention within pathway. B, C, VEGF-induced paxillin phosphorylation (pY118) is reduced by paxillin inhibitor treatment (compound (II-4)). REC treated with VEGF (50 ng/mL) and either inhibitor (1 µM) or vehicle for 4 hrs were lysed. Phosphorylation measured by Western Blot. D, Treated and untreated REC were labeled with Annexin V and PI as in FIG. 9 prior flow cytometric analysis.

FIG. 14: Reduction of pY118 paxillin and increased total paxillin protein in UM cells treated with paxillin inhibitor. A, Representative Western Blot. B, Quantitation of n=4. Metastatic UM (OMM 2.5) cells were treated with HPG at 20 ng/mL or HGF and the paxillin inhibitor (104) for 4 hrs. Lysates were assayed for total and phosphorylated Y1 18 paxillin by Western Blot.

Figure 15:
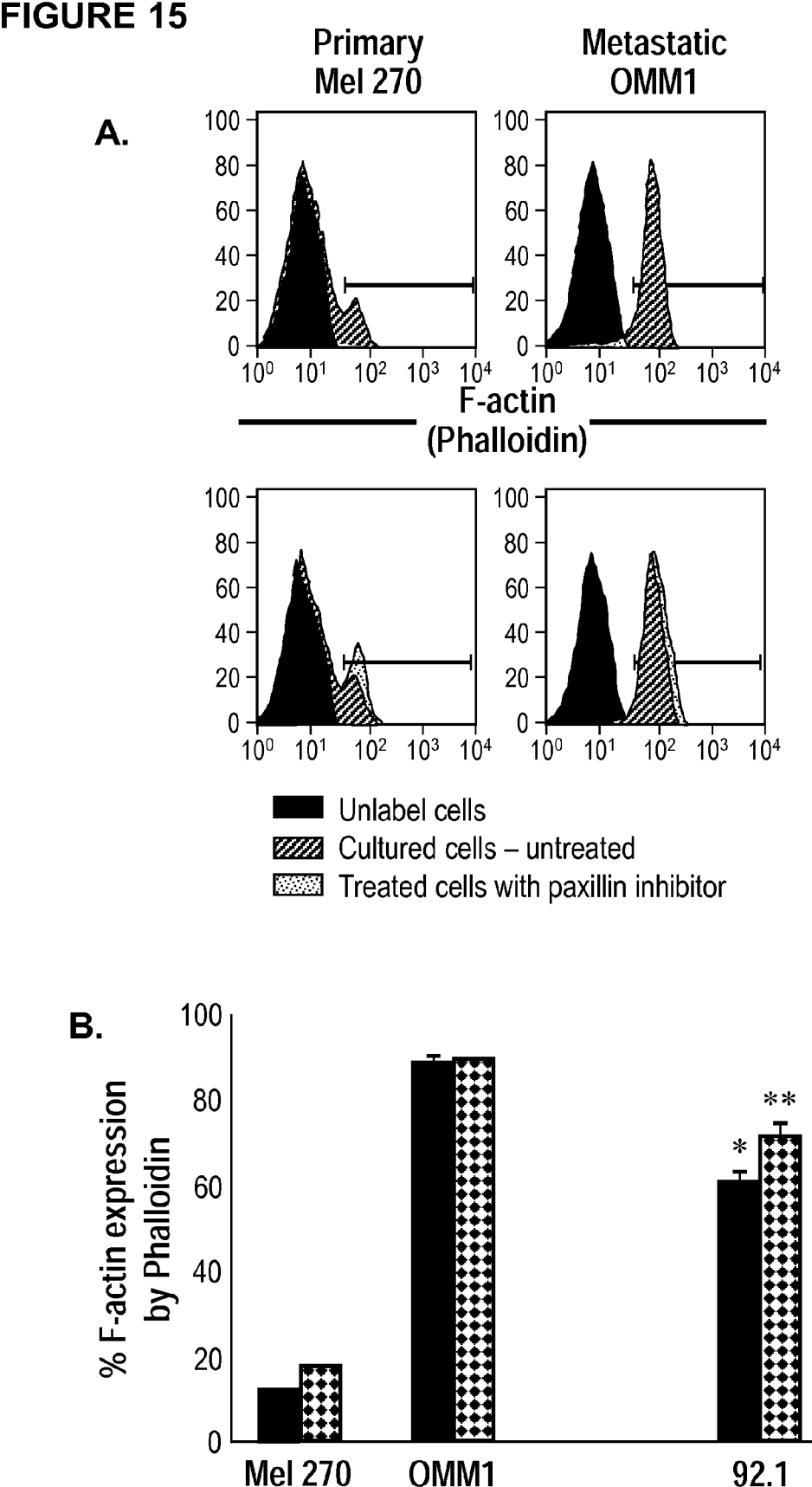
FIG. 15 shows data related to the reduction in proliferation of UM tumor cell lines after treatment with compound (II-4): panel A shows no difference in actin remodeling in the examined UM tumor cells after treatment; panel B shows a similar trend between secondary (metastatic UM) and primary tumor that does not metastasize; panel C shows that modulation of paxillin does not affect VLA-4 protein; and panel D shows the reduction of cellular proliferation in primary UM (Mel 270) cells that become metastatic by paxillin inhibitor.

FIG. 15: The paxillin inhibitor Compound (II-4) selectively affects cellular proliferation of primary UM cells that become metastatic. A. Primary and metastatic UM (Mel 270, OMM 2.1, respectively) cultured cells were intracellularly labeled with phalloidin after +/− paxillin inhibitor treatment for 24 hrs. Unlabeled cells were used to control fluorescence. Histogram representative of n=3. B. Quantitation of experiment +/−SD including primary UM that becomes metastatic (Mel 270), metastatic (OMM 2.1) and primary (92.1) UM cells. *P=0.0007 and **P=0.0005. C. Parallel to experiments from 15A-B, cells were examined for VLA-4 protein levels by flow cytometry. Quantitation of VLA-4 protein levels +/−SD from n=3. D. Reduction of cellular proliferation in primary UM (Mel 270) cells that become metastatic by paxillin inhibitor. CFSE labeled cells were cultured for 96 hrs. Treatment with 1 µM paxillin inhibitor proceeded for the last 24 hrs. Histogram representative of n=3. Analysis performed with Cell Proliferation function from FlowJo.

FIG. 16: Paxillin inhibition reduced pAKT signaling in metastatic UM cells. A, Representative Western Blot of total and phosphorylated paxillin in metastatic UM cells, as in FIG. 4A-B. B, Quantitation from n=3. C, Metastatic OMM 2.5 cells were HGF stimulated in presence or absence of paxillin inhibitor followed by harvest after 4 hrs. Lysates were measured by Western Blot. Representative of n=3. D, Quantitation shows significant reduction of pAKT/AKT after compound (II-4) treatment (P<0.05).

FIG. 17: REC migration. A) Increasing concentrations of compound (II-4) inhibit VEGF-induced migration in a scratch wound assay; [Serum Free-control, VEGF (100 ng/mL), VEGF+100 nM, 500 nM, 10 µM, 100 µM] (IC$_{50}$~180 ηM; n=6/group). Cells were stained with DAPI for representative images. B) RECs seeded onto transwell membranes were stimulated with VEGF+ vehicle or compound (II-4) for 24 hrs. Cells were removed from the topside of membrane and migrated cells were stained with DAPI [Serum-Free (SF), VEGF, +100, +500 nM, respectively]. Cell number was measured using fluorescence microscopy. All data are mean±SD (*, # P<0.001)

FIG. 18: REC Proliferation and Flow cytometry analysis of apoptosis in REC. A) VEGF-induced cellular proliferation was assessed using the WST-1 metabolic assay. Compound (II-4) significantly reduces cellular proliferation. (*P<0.0001). Nuclei were stained with DRAQ5 and imaged to show trend of decreasing proliferation. B) Apoptosis was measured using Annexin V/PI staining Compound (II-4) (1 μM) appears to be non-cytotoxic to retinal endothelial cells after 24 hour incubation (n≈10,000 cells).

FIG. 19: REC attachment assay. Increasing concentrations of compound (II-4) with suspended RECs were seeded to 96-wells to investigate inhibition of REC-adherence to attachment-factor surfaces. Compound (II-4) did not impede the attachment of RECs even at high-concentrations. (P>0.05; n=8).

FIG. 20: VEGF-induced activation of Src/FAK/Paxillin signalsome. A-E) VEGF-induced REC autophosphorylation of FAK Y397 to further induce Src-dependent activation of FAK Y576/577 and Y925. The active Src/FAK complex induces PaxY118 and P-AKT (Ser473). Using a PI3K inhibitor, LY294002 we establish AKT as downstream of Src/FAK/paxillin activation. Src inhibitor, SU6656 inhibited FAK, paxillin and AKT activation. Compound (II-4) (500 nM) reduced Y118 and P-AKT, but not FAK Y925 activation. Neither SU6656 nor compound (II-4) decreased VEGF-dependent activation of ERK1/2, which was shown to be independent of Src-mediated PaxY118 activation (F). All experiments performed in triplicate; *, # P<0.05; data are Mean±SD.

FIG. 21: REC Proliferation. VEGF-induced REC proliferation was inhibited with either Compound (II-4) (500 nM), LY294002 (100¢), SU6656 (10¢), or U0126 (10¢). (*, # P<0.001; Mean±SD, N=8/group).

Figure 22:
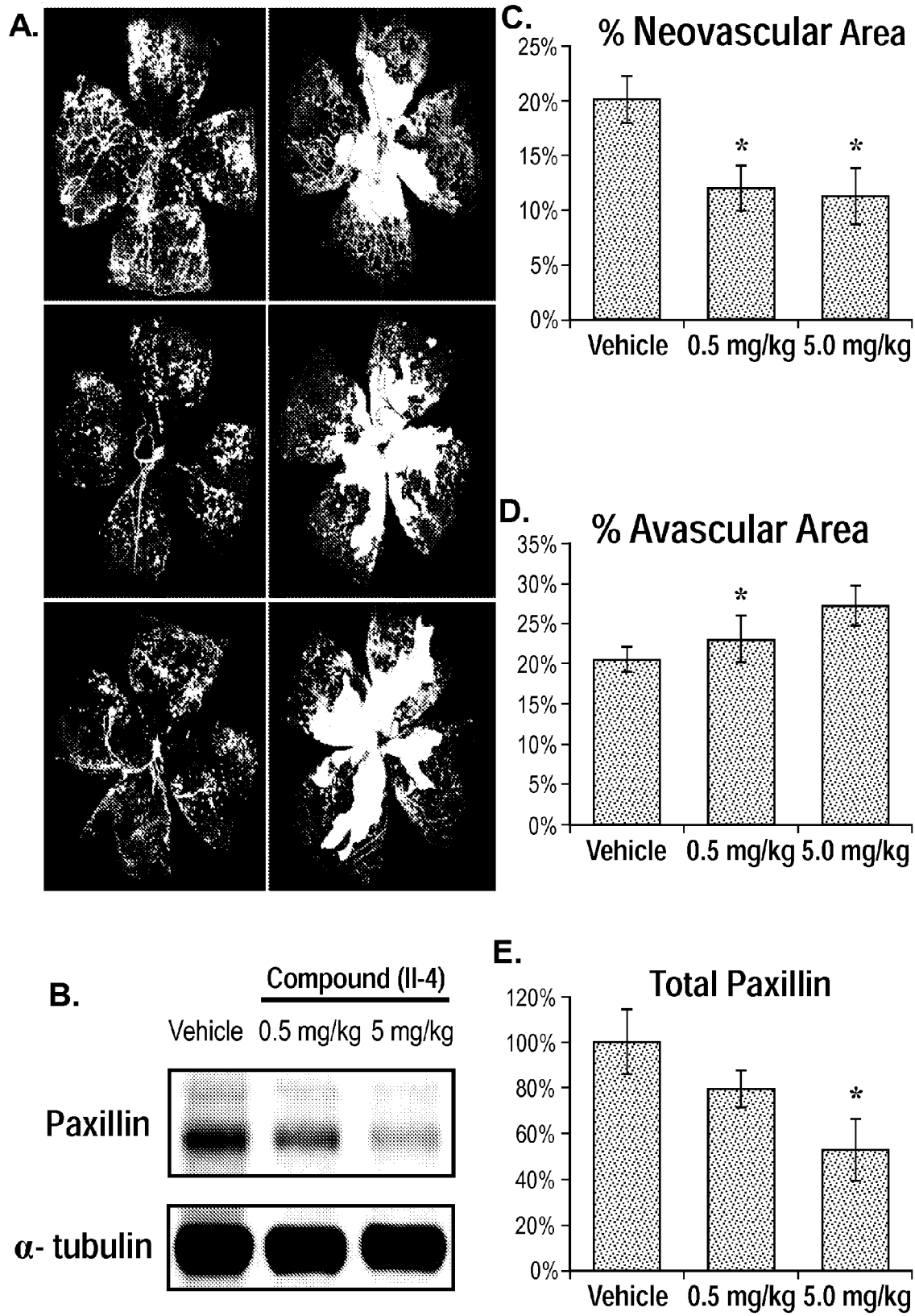
FIG. 22, panel A, shows that compound (II-4) inhibits hypoxia-induced neovascularization and increases retinal avascular area when compared to vehicle controls; panel B shows that compound (II-4) reduces total paxillin protein in retinal homogenates; panel C compares the quantitation of panel A neovascular area; panel D compares the quantitation of panel A avascular area; and panel E compares the quantitation of panel B total paxillin in retinal homogenates.

FIG. 22: Oxygen-Induced Retinopathy (OIR). (A:) P17 retinal whole-mounts were stained for endothelial cells. Representative images of neovascular area (left images) and avascular area (right images) show that compound (II-4) (middle images 0.5 mg/kg and bottom images 5.0 mg/kg; top images vehicle) showed reductions in NV and increases in AV (*P<0.05). Data represent mean (±SD). N=8-14/group. (B): Compound (II-4) reduced total paxillin protein in retinal homogenates (*P<0.05). (C): Quantitation of panel A neovascular area. (D): Quantitation of panel A avascular area. (E): Quantitation of panel B total paxillin.

FIG. 23: Compound (II-4) microsomal stability.

FIG. 24: Cytochrome P-450 interaction studies using human microsomes.

FIG. 25: Off-target screen reveals two binding candidates, 5-HT$_{2B}$ and MT$_1$.

The invention claimed is:

1. A compound having the structure of Formula (I):

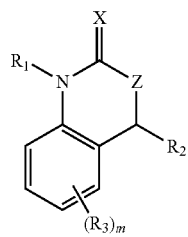

(I)

or a pharmaceutically acceptable salt thereof, wherein:
X is O or S;
Z is O or NH;
R$_1$ is selected from the group consisting of hydrogen, alkyl and arylalkyl;
R$_2$ is 3,4,5-trimethoxyphenyl;
R$_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; or
wherein any two adjacent R$_3$ may combine to form a fused aromatic ring, wherein said fused aromatic ring can be substituted one or more times with R$_4$;
R$_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido; and
m is 0, 1, 2, 3 or 4.

2. The compound of claim 1, wherein R$_3$, independently for each occurrence, is selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido.

3. The compound of claim 1 having the structure of Formula (II):

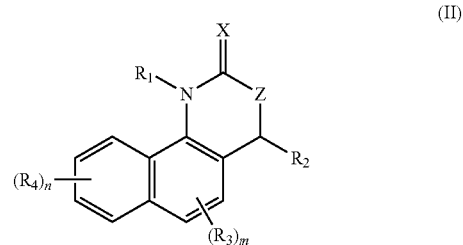

(II)

or a pharmaceutically acceptable salt thereof, wherein:
R$_3$ and R$_4$, independently for each occurrence, are selected from the group consisting of alkyl, alkenyl, alkoxy, trifluoromethoxy, acetyl, aryl, hydroxy, halogen, cyano, nitro, amino, alkylamino, diakylamino, amido, alkylamido and arylamido;
m is 0, 1 or 2; and
n is 0, 1, 2, 3 or 4.

4. The compound of claim 1 wherein R$_1$ is hydrogen.

5. The compound of claim 2, wherein:
R$_1$ is hydrogen;
R$_2$ is 3,4,5-trimethoxyphenyl;
R$_3$, independently for each occurrence, is selected from the group consisting of alkoxy and hydroxy; and
m is 0, 1 or 2.

6. The compound of claim 3, wherein:
R$_3$, independently for each occurrence, is selected from the group consisting of alkoxy and halide; and
R$_4$ is hydrogen.

7. The compound of claim 1, wherein X is O and Z is O.
8. The compound of claim 1, wherein X is O and Z is NH.
9. The compound of claim 1, wherein X is S and Z is O.
10. The compound of claim 1, wherein X is S and Z is NH.
11. The compound of claim 2, selected from the group consisting of:

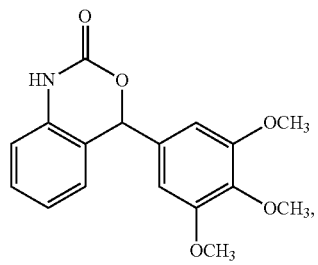

-continued

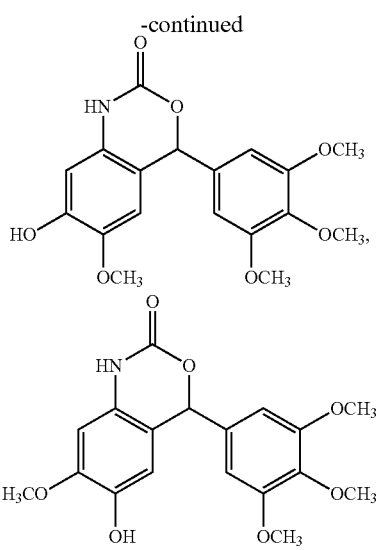

or pharmaceutically acceptable salts thereof.

12. The compound of claim 3, selected from the group consisting of:

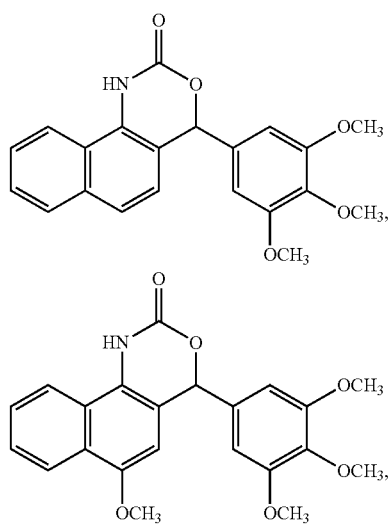

-continued

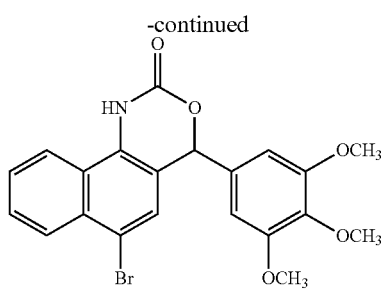

or pharmaceutically acceptable salts thereof.

13. The compound:

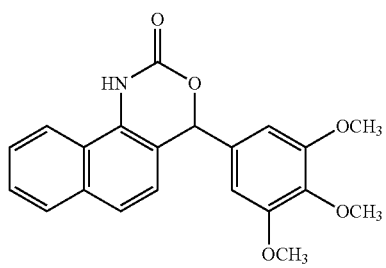 [SMILES: COc1cc(C2OC(=O)Nc3c2ccc2ccccc32)cc(OC)c1OC]

or a pharmaceutically acceptable salt thereof.

14. The compound of claim 1, wherein the compound has (R) stereochemistry.

15. The compound of claim 1, wherein the compound has (S) stereochemistry.

16. A pharmaceutical composition comprising a compound of claim 1 and a pharmaceutically acceptable carrier.

17. A method for the treatment of a disorder selected from the group consisting of metastatic cancer, retinal neovascularization, radiation retinopathy, diabetic retinopathy and polycystic kidney disease in a mammal, comprising administering to the mammal an effective amount of a compound of claim 1.

18. A method of inhibiting paxillin function in a mammal, comprising administering to the mammal an effective amount of a compound of claim 1.

* * * * *

UNITED STATES PATENT AND TRADEMARK OFFICE
CERTIFICATE OF CORRECTION

PATENT NO. : 9,834,525 B2
APPLICATION NO. : 15/116764
DATED : December 5, 2017
INVENTOR(S) : Charles Ryan Yates et al.

It is certified that error appears in the above-identified patent and that said Letters Patent is hereby corrected as shown below:

Applicant(s) should read:
UNIVERSITY OF TENNESSEE RESEARCH FOUNDATION, Memphis, TN (US)

Signed and Sealed this
Twenty-ninth Day of May, 2018

Andrei Iancu
*Director of the United States Patent and Trademark Office*